(12) United States Patent
Huang et al.

(10) Patent No.: US 8,450,086 B2
(45) Date of Patent: May 28, 2013

(54) BACTERIAL MEMBRANE PROTEIN SECRETION

(75) Inventors: Chichi Huang, Radnor, PA (US); Lu Lu, Radnor, PA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 0 days.

(21) Appl. No.: 13/509,287

(22) PCT Filed: Nov. 15, 2010

(86) PCT No.: PCT/US2010/056680
§ 371 (c)(1),
(2), (4) Date: May 11, 2012

(87) PCT Pub. No.: WO2011/062862
PCT Pub. Date: May 26, 2011

(65) Prior Publication Data
US 2012/0225807 A1     Sep. 6, 2012

Related U.S. Application Data

(60) Provisional application No. 61/261,768, filed on Nov. 17, 2009.

(51) Int. Cl.
*A61K 39/42* (2006.01)
*C12P 21/00* (2006.01)

(52) U.S. Cl.
USPC .... 435/69.7; 435/69.8; 435/320.1; 536/23.53

(58) Field of Classification Search
None
See application file for complete search history.

(56) References Cited

U.S. PATENT DOCUMENTS

| | | | |
|---|---|---|---|
| 6,521,427 | B1 | 2/2003 | Evans |
| 6,670,127 | B2 | 12/2003 | Evans et al. |
| 6,753,136 | B2 | 6/2004 | Löhning |
| 6,875,590 | B2 * | 4/2005 | Chen et al. .............. 435/69.7 |
| 7,078,166 | B2 | 7/2006 | Janda et al. |
| 7,393,662 | B2 | 7/2008 | Heavner et al. |
| 2005/0250131 | A1 | 11/2005 | Jestin et al. |
| 2006/0257856 | A1 | 11/2006 | Kang et al. |
| 2006/0286068 | A1 | 12/2006 | Nissen et al. |

FOREIGN PATENT DOCUMENTS

| | | |
|---|---|---|
| WO | WO 2004/002417 A2 | 1/2004 |
| WO | WO 2004/002424 A2 | 1/2004 |
| WO | WO 2005/032460 A2 | 4/2005 |
| WO | WO 2005/081687 A2 | 9/2005 |
| WO | WO 2009/085462 A1 | 7/2009 |
| WO | WO 2009/085464 A2 | 7/2009 |
| WO | WO 2009/085468 A2 | 7/2009 |

OTHER PUBLICATIONS

Se-Ho Kim et al., An approach for preventing recombination-deletion of the 40-50 anti-digoxin antibody VH gene from the phage display vector pComb3. Gene 241 (2000) 19-25.*
Gao, C. et al., "A method for the generation of combinatorial antibody libraries using pIX phage display", Proc Natl Acad Sci USA, vol. 99, pp. 12612-12616 (2002).
Kwasnikowski, et al., "Multivalent display system on filamentous bacteriophage pVII minor coat protein", Journal of Immunological Methods, vol. 307, p. 135 (2005).
Gao, C. et al., Making artificial antibodies: A format for phage display of combinatorial heterodimeric arrays, Proc Nat Acad Sci, vol. 96, pp. 6025-6030 (1999).
Marks et al., By-passing Immunization, Journal of Molecular Biology, vol. 222, pp. 581-597 (1991).
Griffiths et al., "Isolation of high affinity human antibodies directly from large synthetic repertoires", J EMBO, vol. 13, pp. 3245-3260 (1994).
Hoet et al., "Generation of high-affinity human antibodies by combining donor-derived and synthetic complementarity-determining region diversity", Nature Biotechnology, vol. 23, pp. 344-348 (2005).
Klose et al., "The Influence of Amino Substitutions within the Mature Part of an *Eschrichia coli* Outer Membrane Protein (OmpA) on Assembly of the Polypeptide into Its Membrane", The Journal of Biological Chemistry, vol. 263, No. 26, pp. 13297-13302 (1988).
International Search Report for PCT/US10/56680 dated Feb. 17, 2011.

\* cited by examiner

*Primary Examiner* — Kevin Hill
*Assistant Examiner* — Arthur S Leonard
(74) *Attorney, Agent, or Firm* — Brian C. Carey

(57) ABSTRACT

Improved bacterial secretion signals derived from pelB and ompA are provided. The improved variants enhance bacterial membrane secretion are thus useful for production of proteins secreted from bacteria including proteins displayed on filamentous phage particles, and, in particular, proteins requiring oxidative formation of covalent bonds, such as disulfide bonds within or between polypeptide chains in order to form a correctly folded and functional protein structure. Described herein are methods for the multivalent display of complex dimeric proteins on the surface of a bacteriophage particle and combinatorial synthetic libraries of such proteins displayed as a fusion polypeptide with filamentous phage pIX coat protein. Heterodimeric or more complex interchain bonded structures may also be displayed using the method of the invention.

24 Claims, 19 Drawing Sheets

*Fig. 1*
A
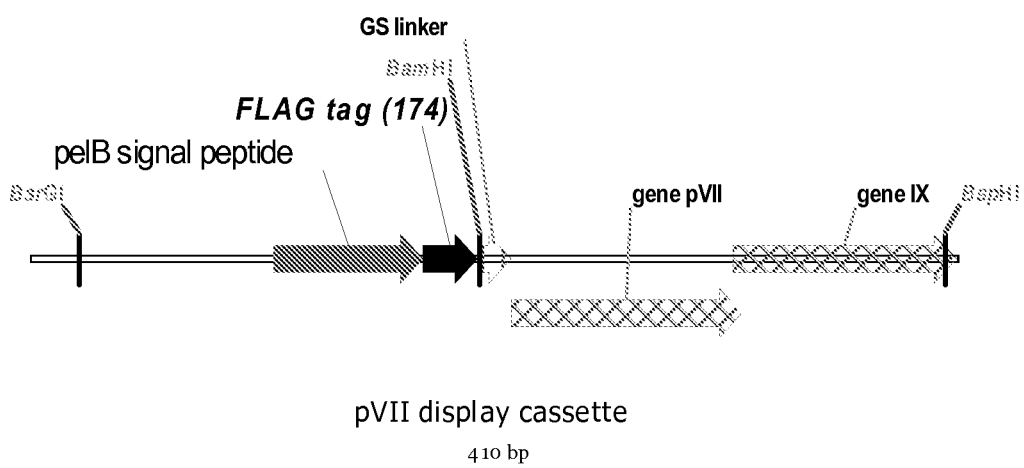
pVII display cassette
410 bp
B
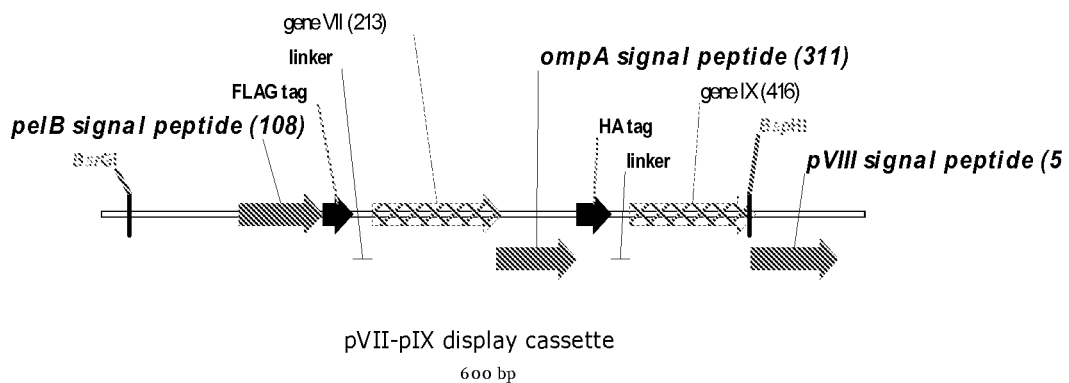
pVII-pIX display cassette
600 bp Fig. 2A-B
2A.
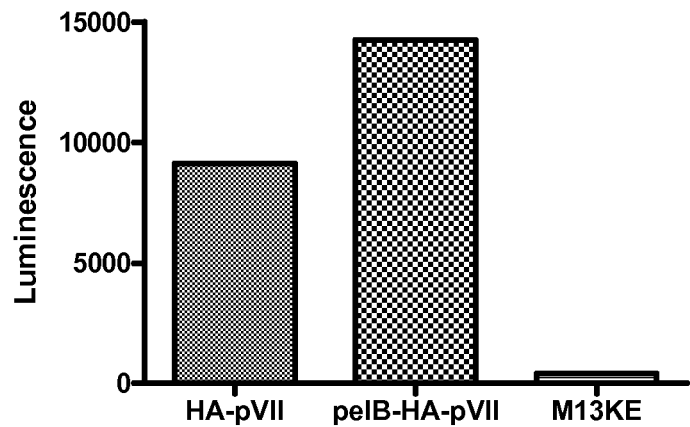
2B.
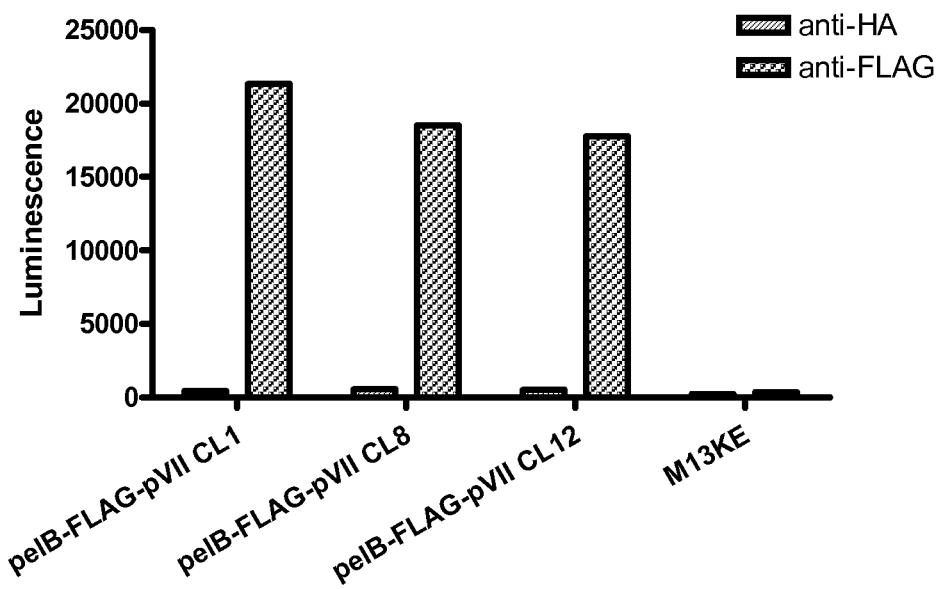

*Fig. 2C-D*
2C.
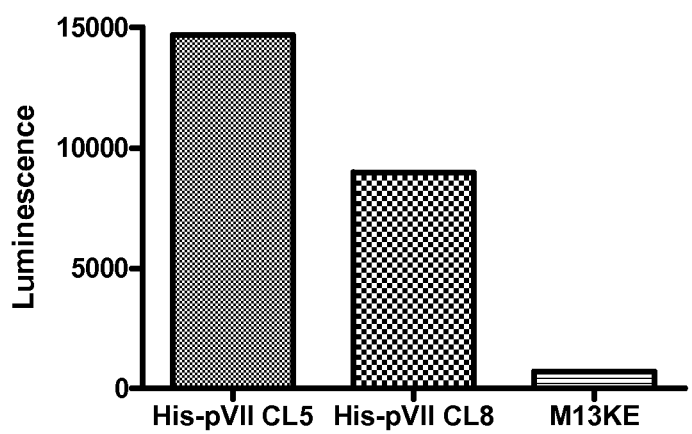
2D.
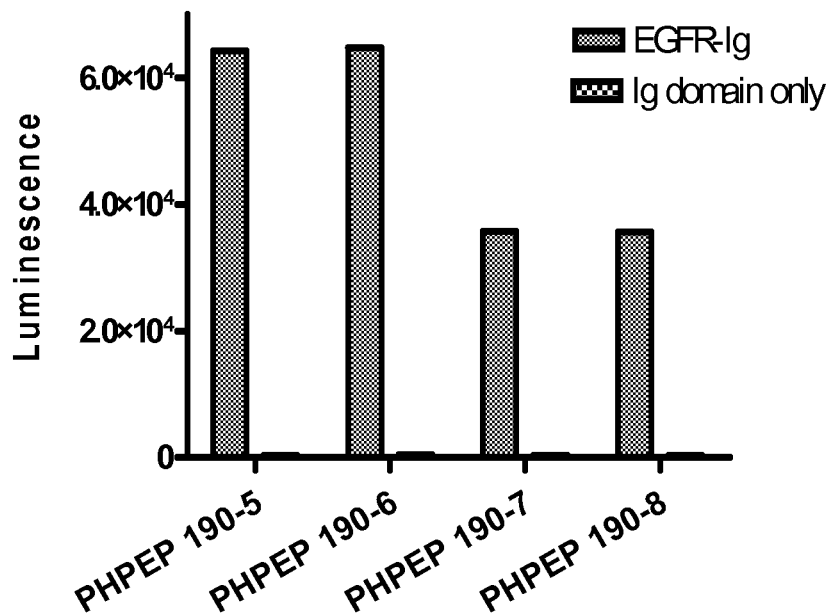

```
WT pelB  ATGAAATACCTGTTGCCTACGGCAGCCGCTGGTTTGTTATTACTCGCGGCCCAGCCGGCCATGGCA
          M  K  Y  L  L  P  T  A  A  A  G  L  L  L  L  A  A  Q  P  A  M  A Mut pelB ATGAAATACCTGTTGTCTACGGCAGCCGCTGGTTTGTTATTACTCGCGGCCCAGCCGGCCATGGCA
          M  K  Y  L  L  S  T  A  A  A  G  L  L  L  L  A  A  Q  P  A  M  A
```

B.

```
WT ompA  ATGAAAAAAACCGCGATTGCGATTGCGGTGGCGCTGGCGGGCTTTGCGACCGTGGCGCAGGCG
          M  K  K  T  A  I  A  I  A  V  A  L  A  G  F  A  T  V  A  Q  A Mut omp  ATGAAAAAAACCGCGATTGCGATTGCGGTGCCGCTGGCGGGCTTTGCGACCGTGGCGCAGGCG
          M  K  K  T  A  I  A  I  A  V  P  L  A  G  F  A  T  V  A  Q  A
```

*Fig. 6*
A.
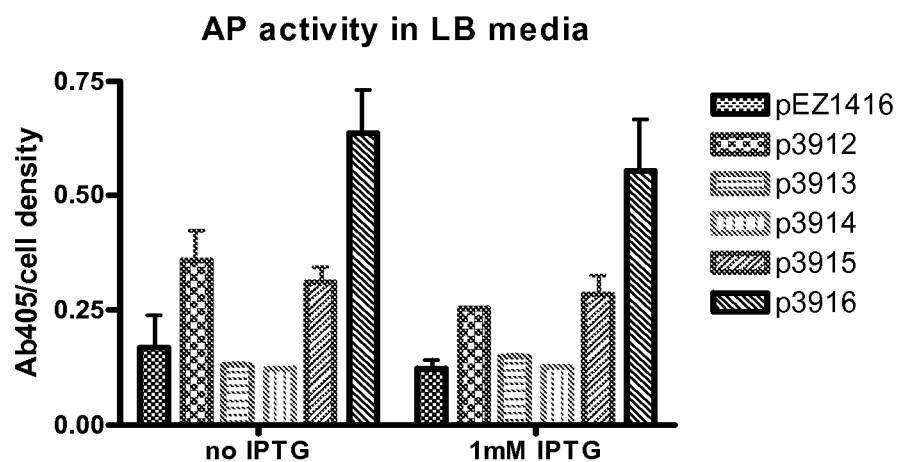
B.
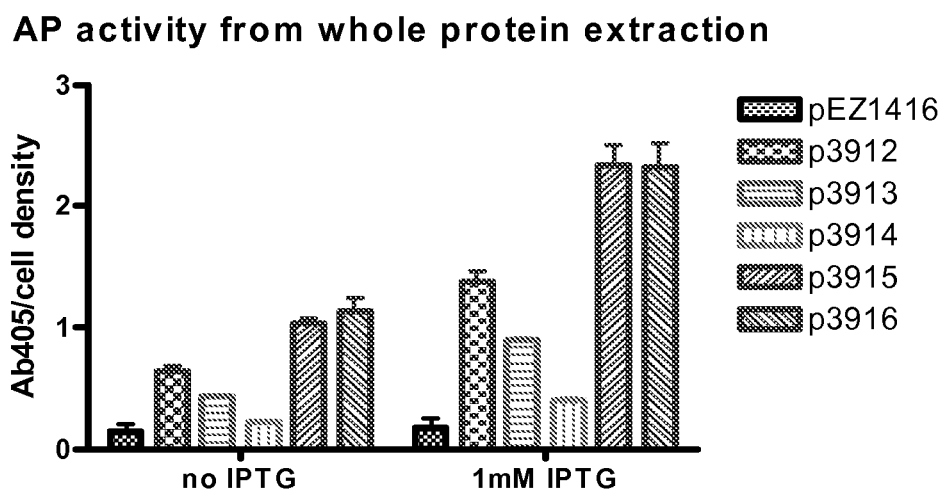

BACTERIAL MEMBRANE PROTEIN SECRETION

CROSS-REFERENCE TO RELATED APPLICATIONS

This application claims the benefit of International Application Number PCT/US2010/056680, filed 15 Nov. 2010, which claims the benefit of U.S. Provisional Application No. 61/261,768, filed 17 Nov. 2009. The entire contents of each of the aforesaid applications are incorporated herein by reference in their entirety.

PRIOR APPLICATION

This application claims priority to U.S. application No. 61/261,768, filed Nov. 17, 2009, which is entirely incorporated by reference.

BACKGROUND

1. Field of the Invention

The invention relates to improved methods for secretion of proteins through the bacterial membrane including the use of filamentous phage coat proteins for display or exogenous proteins including libraries of variants which may be monomeric, dimeric, or heterodimeric or multimeric proteins including complete antibodies and antibody fragments, or other disulfide linked multimeric constructs by coupling a mutant pelB or mutant ompA secretion signal to the exoprotein construct.

2. Discussion of the Field

Filamentous phage display is a widely used technology for affinity-based selection of proteins as each phage particle links the nucleic acid encoding the polypeptide fused to the N-terminus of its coat protein together in the selection process. M13 bacteriophage encodes five coat proteins with approximately five copies of the minor coat proteins pIII and pVI at one end of the phage and the same number of pVII and pIX at other end of the phage. The phage DNA is encapsulated by approximately 3000 copies of the major coat protein, pVIII. Although the display of foreign polypeptides has been accomplished with each of the coat proteins of M13, pIII and pVIII are by far the most common fusion partners. Using this technique, libraries of peptides, Fabs, scFvs and other protein binders have been constructed and found use in diverse applications and with great commercial value.

The pIII coat protein has been favored over the other proteins is due to its length and conformation. The pIII minor coat protein is a 402 amino acid, 42 kD protein responsible for phage infection into *E. coli* comprising two domains connected by a flexible hinge. Fusions to the pIII N-terminus tether the displayed protein away from the phage particle reducing its ability to interfere with required pIII functions and further providing adequate access for ligand binding. In contrast, pVII and pIX are short helical proteins of 33 and 32 aa, respectively, closely packed in the phage particle. Nevertheless, there have been reports describing the display of scFv libraries on pIX (Gao, C. et al. Proc Natl Acad Sci USA 99, 12612-12616, 2002) and heterodimeric display of Fv or Fab libraries by taking advantage of the ability to fuse different polypeptides to both pVII and the closely adjacent pIX (Gao, et al. 1999 Proc Nat Acad Sci 96: 6025-6030 and Janda U.S. Oat. No. 7,078,166). Phage displaying pVII fusions have also been reported (Kwasnikowski, et al. 2005. J Immunol Methods 307:135). Using a hybrid phage vector or phagemid vectors peptides, Fab, and other proteins can be displayed on phage fused to the pIX coast protein (WO2009/085462, WO2009/085464, and WO2009/085468). An alternative approach in which exoproteins encoded by the phage or phagemid vector are not fused to the coat protein but rather covalently attach to re-engineered coat proteins pIII and pIX with through disulfide bonding has also been described (U.S. Pat. No. 6,753,136).

*Escherichia coli* is one of the most widely used hosts for the production of recombinant proteins. However, there are often problems in recovering substantial yields of correctly folded proteins. One approach to solve these problems is to have recombinant proteins secreted into the periplasmic space or culture medium. The secretory production of recombinant proteins has several advantages, such as simplicity of purification, avoidance of protease attack and N-terminal Met extension, and a better chance of correct protein folding.

After DNA replication and expression of phage proteins, M13 and other filamentous phage are assembled at the bacterial host cell membrane. The transport of the phage structural proteins into the membrane is a crucial step for phage assembly. In the practice of phage display, bacterial signal peptides have been widely used in constructs to help transport fusion proteins through the membrane and, have been critical to achieving display of certain of types of fusion proteins. The signal peptide of pectate lyase B (pelB) from *Erwinia carotovora* has been widely utilized in for the purpose of both enhancing protein production using bacterial cells as well as in phage display.

The ability to display a more diverse and complex proteins such as dimeric proteins by bacterial culture or on the surface of a phage particle using bacterial host cells and in a combinatorial library format is advantageous in being able to perform selections of modified and re-engineered complex protein structures. There is a continuing need to advance the art for generating highly efficient protein production methods as well as high throughput methods of screening variants of complex proteins such as that of the human IgG, which is a homodimer of heavy and light chain pairs (heterodimers) connected via intermolecular disulfide bonds.

SUMMARY OF THE INVENTION

The present invention provides an improved method for the expression, translocation, and assembly of exogenous proteins in bacterial membranes, such as on phage particles being assembled in bacterial hosts, by incorporating nucleic acids encoding a mutant pelB signal sequence operably fused to the nucleic acids encoding the amino acid sequence of the peptide or polypeptide sequence desired to be expressed and/or displayed, the mutant pelB signal of the sequence MKYLLSTAAAGLLLLAAQPAMA which is the P6S variant of (SEQ ID NO: 1). In one aspect of the invention, the sequence encoding the mutant pelB signal may be the mutant SEQ ID NO: 2 in which the base at position 16 is thymidine. In another embodiment of the invention, the secretion signal encoded is a mutant ompA of the sequence MKKTAIAIAVPLAGFATVAQA which is the A11P variant of the wild type sequence (SEQ ID NO: 3). In one aspect, the sequence encoding the mutant ompA secretion signal may be the mutant SEQ ID NO: 4 in which the base at position 31 is cytidine. In a method of the invention, the secretion signal P6S of SEQ ID NO: 1 is used to enhance protein translocation in a bacterial cell culture.

The invention provides improved methods for multivalent display of proteins on phage particles and means for display of dimeric, or multimeric proteins on phage particles fused to phage coat proteins. In one embodiment, the multivalent display is of an exoprotein fused to the N-terminus of the phage pVII or pIX minor coat protein. The embodiments further encompass the expression and display of two different exoproteins simultaneously on a phage particle where the first protein is fused to pVII and the second protein is fused to pIX by fusing a sequence encoding the secretion signal P6S variant of pelB (SEQ ID NO: 1) to the exoprotein encoding region of the pIX or pVII fusion protein which is a phage or phagemid vector. In one aspect, the polypeptides fused to pVII or pIX may form interchain associations to form higher order structures, such as dimeric or multimeric pVII-tethered proteins or dimeric or multimeric pIX-tethered proteins on phage, or dimeric or multimeric structures in which one or more exoproteins is fused to one phage coat protein and the same or different exoprotein is fused to an different phage coat protein. The multimeric proteins may form disulfide linkages between the polypeptide chains fused to the phage coat protein or form more complex structures as by association with a separately encoded and expressed exoprotein. In one example of a dimeric, disulfide-bonded structure, the protein formed comprises an antibody Fc domain with interchain disulfide bonds and intrachain disulfide bonded domains capable of binding to Fc-receptors, protein A, or complement factor C1q. In one aspect, the protein structure formed from coat protein fused polypeptide chains further associate with an antibody light chain to form a full IgG molecule. In another embodiment, two different polypeptides are displayed as pVII and pIX fusion, where the polypeptides may form interchain associations on the filamentous phage of a noncovalent or covalent nature to form dimeric or multimeric protein structures.

The invention provides for the enhanced growth of phage expressing an exoprotein fused to a coat protein selected from the group consisting of pIII, pVII, pVIII, or pIX in culture by incorporating a secretion signal encoding region selected from SEQ ID NO: 2 and 4 or a sequence encoding the peptide of SEQ ID NO: 1 or 3 fused to the exoprotein encoding region.

The invention provides a replicable vector coding for at least one fusion protein, having an nucleic acid sequence encoding an exogenous polypeptide fused to a sequence encoding a phage coat protein selected from the group consisting of pIII, pVII, pVIII, or pIX wherein a secretion signal encoding sequence encoding the P6S variant of SEQ ID NO: 1 or the [A11P] variant of SEQ ID NO: 3 is fused to the exoprotein encoding sequence. In an embodiment of the invention, the vector encoding the protein phage coat protein fusion includes additional sequence interposed between the protein encoding a protein tag recognizable by a ligand or antibody, a protease cleavage site, or a electrostatically charge region, or a region capable of chemical conjugation such as a lysine residue. In one aspect, the additional sequence is an HA sequence (SEQ ID NO: 5), a Flag (SEQ ID NO: 6) region, or hexahistidine (His6, SEQ ID NO: 7).

In another aspect of using the secretion signals of the present invention, the signals are used to construct phage or phagemid vectors with variegated regions with the exoprotein encoding sequences for the purpose of displaying a library of variant proteins. In a preferred embodiment the exoprotein portion of the fusion protein is an antibody or fragment thereof and the library so formed is an antibody or antibody fragment, e.g. scFv or Fab, library. In one aspect of the invention the variant secretion signals are used to construct libraries of a homodimer-forming polypeptide chain, such as an Fc-fusion protein. In another embodiment, the homodimeric structure may further associate with a heteropolypeptide to form a more complex structure. In one aspect, the display of both an antibody heavy chain polypeptide and a light chain polypeptide in a single phage molecule results in the assembly of a functional antibody molecule at the surface of the phage particle, such as, but not limited to a complete IgG molecule. Included in the invention are host cells containing the replicable vector and a phage particle which is capable of displaying the fusion polypeptide on the surface of the phage as a dimeric disulfide-linked protein. The libraries so generated may display a de novo library useful for assembly, screening and such other interrogative techniques as are practiced in the art, for selection and improvement of antibody compositions.

BRIEF DESCRIPTION OF THE SEVERAL VIEWS OF THE DRAWING

FIG. 1A-B are diagrams of the cloning cassettes used to express pVII fusion proteins (A) or for dual expression of pVII and pIX fusion proteins (B).

FIG. 2A-E show the results of the phage ELISA for specific binding of antibodies to phages displaying HA (A), FLAG (B), His-6 (C), and the specific binding of a soluble dimeric EGFR-Ig construct to phages displaying PHPEP 190 (D) and the specific binding of the streptavidin to phages displaying PHPEP 97 (E); where M13KE phage was used as the negative control.

FIG. 5 shows the sequences of the signal peptides used in the present studies and the positions of the mutations causing single amino acid changes in each expressed sequence: Pro to Ser on position 6 of pelB (A) and Ala to Pro on position 11 of ompA (B) were identified on the recombinant phage in later generation with normal plaque size and high growth titer.

FIG. 6A-B are assays for the activity of alkaline phosphatase (AP) secreted from bacterial cultures grown in LB (A) or remaining in the bacterial pellet (B) where one of the four sequences was fused to the coding sequence: wild type signal peptide pelB (p3915), ompA (p3913), and M13 gene III (p3912) and mutated pelB (p3916) and ompA (p3914). The secreted AP in LB media and total AP expressed in cell lysates were measured with AP substrate and normalized with cell density.

BRIEF DESCRIPTION OF THE SEQUENCE LISTING

Figure 2E:
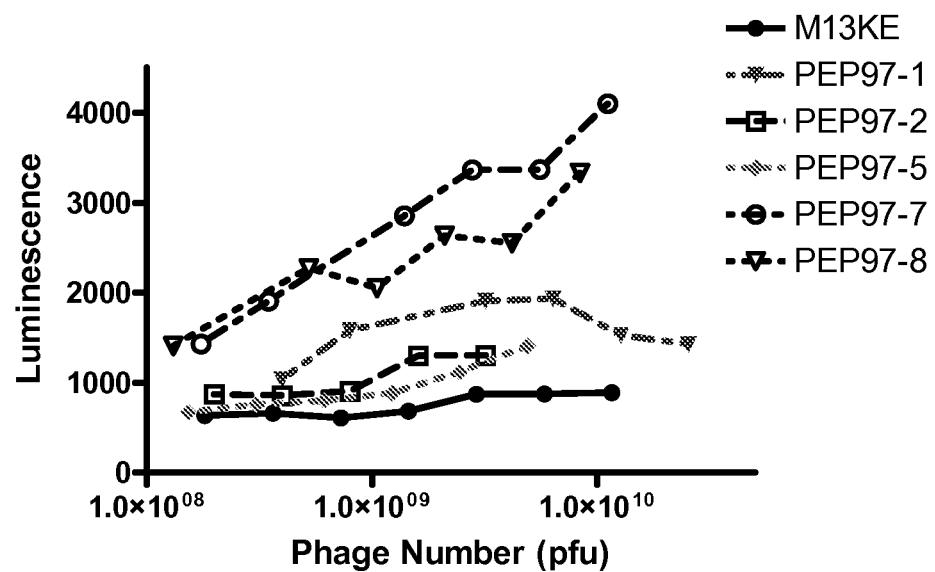

| SEQ ID NO: | Description | Features |
|---|---|---|
| 1 | pelB including variant | P6S |
| 2 | pelB coding sequence for WT and variant | C16T |
| 3 | ompA including discovered variant | [A11P] |
| 4 | ompA coding sequence for WT and variant | G31C |
| 5 | HA | |
| 6 | FLAG | |
| 7 | 6xHis | |
| 8 | PHPEP 190 | |
| 9 | PHPEP 97 | |

DETAILED DESCRIPTION OF THE INVENTION

Abbreviations

ADCC=antibody-dependent cell-mediated cytotoxicity, ADMC=antibody-dependent monocyte-mediated cytotoxicity, c1q=complement factor 1q, EPO=recombinant erythropoietin, FcR=Fc receptor; Ig=immunoglobulin; Hc=heavy chain; Lc=light chain; IPTG=isopropylthio-β-galactoside; ompA=gene encoding the E. coli outer membrane protein A; pelB=gene encoding the pectate lyase gene of E. caratovora Definitions As used herein, unless otherwise indicated or clear from the context, antibody domains, regions and fragments are accorded standard definitions as are well known in the art. The proteins of the invention are derived from, or incorporate portions of antibodies of one or more immunoglobulin classes. Immunoglobulin classes include IgG, IgM, IgA, IgD, and IgE isotypes and, in the case of IgG and IgA, their subtypes, e.g. $IgG_1$, $IgG_2$, $IgG_3$, and $IgG_4$.

By "cistron" is meant a sequence of nucleotides in a DNA molecule coding for an amino acid sequence and including upstream and downstream DNA expression control elements.

By "exogenous polypeptide" or "exogenous protein" or "exoprotein" is meant a protein not normally encoded by the wild-type filamentous phage genome, but rather is foreign to the normal phage protein. A typical exogenous polypeptide is any polypeptide of interest, including an antibody immunoglobulin heavy chain (Hc) domain or immunoglobulin light chain (Lc) domain, an immunoglobulin heavy chain variable domain ($V_H$), an immunoglobulin light chain variable domain ($V_L$), natural or synthetic polypeptides, a single chain antibody (scFv), or a sequence or combination of immunoglobulin domains such as they occur in nature especially as an Fc domain which may include CH3, CH2, a hinge region and/or a CH1 domain or fragment thereof.

By "Fc", a label given the crystallizable cleavage fragment of a papain digested IgG; is meant a functional fragment of an antibody comprising a dimeric structure of polypeptide chains derived from antibody constant domains and having interchain linkages of disulfide bonds. In human IgG1, papain creates a fragment C-terminal to Cys226 (numbered using the EU index as in Kabat et al., *Sequences of Proteins of Immunological Interest*, 5th Ed. Public Health Service, National Institutes of Health, Bethesda, Md. (1991), which is expressly incorporated herein by reference. The "EU index as in Kabat" refers to the residue numbering of the human IgG1 EU antibody. Although the definition of N-terminal residue of the Fc may vary, it is generally appreciated to include at least residue 223 in the Kabat numbering system, which is the third residue N-terminal to the first interchain bonding cysteine (C226 in the Kabat system). The Fc portion of the molecule is not directly involved in contact of the antibody with its specific target antigen, but mediates effector functions. These functions are of two types: (1) functions that require binding of the antibody to an antigen, such as C1q binding and/or complement dependent cytotoxicity (CDC) activity or ADCC and ADMC following Fc-receptor gamma-type binding for IgG, Fc-receptor epsilon binding for IgE, and Fc-receptor alpha binding for IgA; and (2) functions that are independent of antigen binding such as persistence in the circulation by the ability to bind FcRn and be transcytosed across cellular and tissue barriers (such as the gut). The ability to significantly increase the serum half-life of antibody molecules or other molecules via the fusion of an Fc, in particular, is highly advantageous. Longer lived molecules may reduce the amount needed in clinical treatments, thereby reducing and frequency of administration.

The terms "Fc receptor" or "FcR" are used to describe a receptor that binds to the Fc region of an antibody. FcR include FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (FAM) in its cytoplasmic domain. Inhibiting receptor FcγRIIB contains an immunoreceptor tyrosine-based inhibition motif (ITIM) in its cytoplasmic domain (see review in Daëron, Annu. Rev. Immunol., 1997, 15:203-234; FcRs are reviewed in Ravetch and Kinet, Annu. Rev. Immunol., 1991, 9:457-92; Capel et al., Immunomethods, 1994, 4:25-34; and de Haas et al., J. Lab. Clin. Med., 1995, 126:330-41, each of which is incorporated herein by reference).

By "fusion polypeptide" or "fusion protein" is meant a fusion polypeptide (protein) comprising first and second polypeptides encoded by first and second nucleic acid sequences, respectively, which are operatively linked (fused). As exemplified herein, fusion proteins displayed on phage particles are fusions of an exoprotein, a protein not native to the phage proteome, and a phage coat protein.

The term "library" denotes a collection of encoded proteins which are variants, that is, where certain regions are the same or similar and other regions vary. The variation regions may be by directed or random variation (stochastic or non-stochastic changes). A library or variants can be described in terms of number of different variants or "size" of the library. A useful de novo antibody library has high diversity ($>10^{10}$), amenable to alteration, easy to assemble, and have a low background of undesired sequences. Coupling the following methods accelerates library assembly and leads to low background: (a) Kunkel-based single-stranded mutagenesis; (b) palindromic loop with restriction site and; (c) use of a megaprimer approach.

A "dimeric protein" or "multimeric protein" as used herein refers to more than one separate polypeptide or protein chain associated with each other to form a single globular protein in vitro or in vivo. The multimeric protein may consist of more than one polypeptide of the same kind to form a "homodimer" or a "homomultimer." Alternatively, the multimeric protein may also be composed of more than one polypeptide of distinct sequences to form a "heterodimer" or "heteromultimer." Thus, a "heteromultimer" is a molecule comprising at least a first polypeptide and a second polypeptide, wherein the second polypeptide differs in amino acid sequence from the first polypeptide by at least one amino acid residue. The heteromultimer can comprise a "heterodimer" formed by the first and second polypeptide or can form higher order tertiary structures where more than two polypeptides are present. Exemplary structures for the heteromultimer include heterodimers (e.g. Fab, Fc fragments, and diabodies), trimeric G-proteins, heterotetramers (e.g. F(ab')2 fragments and IgG) and further oligomeric structures.

A "phagemid" or "phage vector" is a replicable cloning vector that contains components derived from both phage chromosomes and exogenous DNA such as that from plasmids. As the phagemid contains a portion of a phage genome, upon co-infection of the host with a helper phage, it can be packaged into phage particles. A phagemid of the invention can be packaged into phage M13 particles.

The term "surface of a phage particle" refers to the part of a bacteriophage particle which is in contact with the medium in which the particle is contained. The surface of the phage particle is determined by the coat protein assembly (the assembled members of the protein coat of the particle) and inner face of the coat protein assembly bounds the region containing nucleic acids of the phage replicated during production of phage in an appropriate host cell.

By "phage coat protein" is meant those proteins forming the phage coat of naturally occurring bacteriophages. In filamentous bacteriophage, such as f1, fd, and M13, the coat proteins are gene III protein (pIII), gene VI protein (pVI), gene VII protein (pVII), gene VIII protein (pVIII), and gene IX protein (pIX). The sequences of the coat proteins of M13 as well as the differences between the closely related members of the filamentous bacteriophages are well known to one of ordinary skill in the art (see, e.g., Kay, B. K., Winter, J. & McCafferty, J., eds. (1996). Phage display of peptides and proteins: a laboratory manual. Academic Press, Inc., San Diego).

Overview

In creating fusion proteins to phage coat proteins, the exoprotein molecule can be large or of diverse chemical characteristics relative to the phage coat protein, particularly so with respect to pIX or pVII, and may interfere with assembly of recombinant phage particles. In order to avoid assembly interference, a phagemid system has often been used whereby the phage particles assemble in the presence of a helper phage and therefore contain both expressed wild-type and exoprotein-coat protein fusions. Phagemid systems are more cumbersome because of the extra steps required and result in much less than the full complete complement of coat protein, if any, displaying the exoprotein. For the latter reason, phagemid display systems are typically considered monovalent. On the other hand, use of a phage vector system to achieve multivalent display often causes low titer phage growth.

The present invention is based on the discovery that a single nucleotide mutation in the coding sequence for the pectate lyase B secretion signal from *Erswinia carotovora* (pelB) of C for T in the first base of the codon for the sixth residue of the sequence, resulting in a proline to serine change in the encoded signal (SEQ ID NO: 1), causes an improvement in the secretion of several proteins from a bacterial host membrane including proteins displayed on M13 phage coat proteins presumably by improving the secretion of peptides and proteins to the periplasmic region. Secondly, a mutation in the ompA secretion signal, the A11P variant of SEQ ID NO: 3, has been shown to enhance the titer of phage displaying peptide-coat protein fusions.

Using the P6S pelB variant secretion signal, applicants have demonstrated that peptides; including heavily positive-charged, negative-charged or disulfide bond constrained peptides, may be successfully displayed on pIX and pVII phage coat proteins and that antibody fragments and, more recently, dimeric antibody structures including whole IgG can be successfully displayed as a fusion protein of the pIX coat protein using a phagemid system. In addition, as exemplified herein, using the P6S pelB and the ompA, a variety of different peptides and a small protein domain, can be multivalently displayed fused to pVII using a phage vector as described herein. The successful and efficient display of large and multimeric proteins on pIX was undertaken using the presently described mutant pelB secretion signal (SEQ ID NO: 1). The simultaneous multivalent display of proteins on pVII and pIX described herein employed a mutant pelB secretion signal (SEQ ID NO: 1) and an ompA secretion signal (SEQ ID NO: 3), however, either the pelB secretion signal or the ompA secretion signal may be used in conjunction with both proteins to be multivalently displayed and phage coat protein fusions.

These results indicate that the system encompassing the mutant pelB signal sequence discovered and reduced to practice using exoprotein display on pIX or pVII coat proteins using a phagemid vector or a phage vector, can be used to display biochemically diverse peptides and proteins. In addition, other proteins which comprise globular scaffolds such as the fibronectin domains of fibronectin, titin and the like; Z-domain of protein-A, Ankyrin repeat, PDZ-domains, Knottins, CTLA-4 extracellular domain, and the like may be displayed using this system. Monomeric, dimeric, or multimeric receptor proteins such as those that bind to growth factors (e.g. the erythropoietin receptor and the ERBB family of receptors including heregulin), neurotransmitter receptors (e.g. γ-Aminobutyric acid), and other organic or inorganic small molecule receptors (e.g. mineralocorticoid, glucocorticoid) are examples of exoproteins that may be displayed using vectors encoding the mutant sections signals selected from SEQ ID NO: 1 and 3 coupled to the coding sequences for the polypeptide chains comprising the wild type, mutant, or truncated receptor polypeptide chains. Preferred heterodimeric receptors are nuclear hormone receptors (Belshaw et al. (1996) *Proc. Natl. Acad. Sci. U.S.A* 93 (10): 4604-4607), erbB3 and erbB2 receptor complexes, and G-protein-coupled receptors including but not limited to opioid (Gomes et al. (2000) *J Neuroscience* 20 (22): RC110); Jordan et al. (1999) *Nature* 399:697-700), muscarinic, dopamine, serotonin, adenosine, and $GABA_B$ families of receptors. Further, using standard techniques for randomization and variegation, the construction of display vectors for the above mentioned monomeric, dimeric, or multimeric proteins can serve as the basis for construction of libraries of variant molecules displayed on phage. Such libraries can be useful tools for the exploration of protein remodeling and re-engineering based on these motifs and scaffolds.

The applicants of the present invention have unexpectedly successfully displayed antibody components as described herein a fusion protein to pIX or pVII coat protein on the surface of a filamentous phage particle in as a homodimeric disulfide linked protein displaying at least one of the known biologic activities of the Fc-domain of a natural antibody, such as Fc-receptor binding, and, when in the form of a bivalent antigen-binding protein, capable of specific binding to target antigen. The ability to express large, multidomain proteins tethered to phage coat proteins has heretofore not been reported and is believed to be solely or in part due to the use of the mutant pelB secretion signal in the exoprotein construct.

Method of Making the Invention

In the fusion protein displayed on a filamentous phage particle, the "fusion" between the exogenous polypeptide and the filamentous phage coat protein, and in particular the pVII or pIX coat protein, may be directly linked by a amide linkage, or may comprise a linker polypeptide (i.e., a "linker"). Any of a variety of linkers may be used which are typically a stretch of about 5 to 50 amino acids in length. Particularly preferred linkers provide a high degree of mobility to the fusion protein at the point of the linker. Linkers devoid of secondary structure such as those comprised of predominantly glycine (G, Gly) residues, such as those having G4S (Gly-Gly-Gly-Gly-Ser) repeats or G3S (Gly-Gly-Gly-Ser) where the number of repeats is typically from one to twelve, may be used for this purpose.

The first polypeptide is an exogenous protein and the second polypeptide is a filamentous phage coat protein, such as pVII or pIX protein, whereby the exogenous protein is fused to the amino terminus of the filamentous phage protein. Further, when the fusion protein is in the immature form, i.e., where the leader sequence has not been processed (removed), a fusion protein may contain the amino terminal prokaryotic secretion signal variants of pelB or ompA as described herein.

Where it is desired to express an antibody (immunoglobulin) molecule, a polynucleotide molecule encoding the immunoglobulin will comprise: (1) a first cistron comprising a translational initiation region and a secretion signal operably fused to a polynucleotide sequence encoding a heavy chain and (2) a second cistron comprising a translational initiation region and a secretion signal operably fused to a polynucleotide sequence encoding a light chain, wherein upon expression of the light and heavy polypeptide chains in a prokaryotic host cell, the light and heavy chains are folded and assembled to form a biologically active immunoglobulin. Where it is desired to express the antibody or at least the portions of an antibody capable of stably associating to form a dimeric or heterodimeric structure on the surface of a phage particle, one or both of the cistrons will code for a fusion protein comprising a mutant secretion signal of the invention selected from SEQ ID NO: 1 and 3, fused to an immunoglobulin domain, and which is fused to a phage coat protein.

In natural antibodies, the light chain polypeptide and the heavy chain polypeptide chains are encoded and expressed separately. The typical heterodimeric structure of the IgG class of molecules is dependent on the proper assembly of and formation of disulfide linkages among and between the four polypeptide chains, two heavy and two light chains, of the molecule. Thus, in the present invention, the assembly of the dimeric Fc-portion of the antibody and/or the association of the light chains, when present, recapitulates the natural process of antibody formation insofar as the individual domains of the protein self-associate and form disulfide linkages therebetween.

In one embodiment, the Fc-containing protein to be displayed on the surface of the filamentous phage particle is a natural antibody and a dicistronic vector is constructed for the expression of a Fc-construct-pIX or Fc-construct-pVII fusion protein and a separately encoded and expressed antibody Lc or antigen binding domain which will self-associate. Antigen-binding proteins of the invention can have binding sites for any epitope, antigenic site or protein. Preferred antigen-binding proteins neutralize activation of receptor proteins by direct binding to the receptor or by binding and neutralization of their cognate ligand(s). Generally, the antigen binding domain will be formed of an antibody Lc and an antibody Hc variable domain fused to the natural antibody Hc sequence comprising the Fc domains. In another embodiment, the coat protein-fusion protein includes a scFv linked to the Fc-domain. In another aspect of the invention, the antigen binding sites of the heavy and light chains comprising the scFv may be varied to provide two different binding specificities thereby making the self-assembled disulfide linked construct protein displayed in the phage surface a bispecific and bivalent molecule. For example, substituted for the $V_L$ and $V_H$ domains of an IgG molecule are scFv domains of different specificity such that the resulting molecule, and is capable of binding to two different epitopes simultaneously. Other methods of creating bispecific antibody molecules having multiple variable domain pairs are taught in US20020103345A1 which could be displayed on phage particles using the methods of the present invention incorporated herein by reference.

In one embodiment the antigen binding or receptor binding domain is not derived from an antibody domain but is a known or random peptide sequence fused to the Fc-domain. Applicants co-pending applications WO04/002417; WO04/002424; WO 05/081687; and WO05/032460 describe a structure referred to herein as a MIMETIBODY™ structure, each of which references are entirely incorporated herein by reference, and which structures are included as dimeric disulfide-linked structures which may be fused to the pIX or pVII phage coat protein and displayed on the outer surface of the phage particle.

In one embodiment, the protein displayed on the phage particle comprises a pair of bioactive peptide-linker-hinge-CH2-CH3 polypeptides, the pair linked by association or covalent linkage, specifically, a Cys-Cys disulfide bond. The bioactive peptide may be on any length and be a naturally occurring sequence derived from any species or be an artificial sequence. The peptides will generally be encoded by the phagemid vector and fused to the Fc-portion of the construct for display on the phage particle. Other constructs of similar structure may be expressed using vectors incorporating the mutant secretion signals of the present invention where the peptide has no known bioactivity but it present to function as marker, a tag, an antigen, or provides for conjugation of a reporter group, a chelating group, or the like.

The level of expression of secreted protein or coat protein-fusion protein can additionally be controlled at the transcriptional level. The fusion proteins are under the inducible control of the Lac Z promoter/operator system (see FIG. 1). Other inducible promoters can work as well and are known by one skilled in the art. For high levels of surface expression, the suppressor library is cultured in an inducer of the Lac Z promoter such as isopropylthio-β-galactoside (IPTG). Inducible control is beneficial because biological selection against non-functional pIX fusion proteins can be minimized by culturing the library under non-expressing conditions. Expression can then be induced only at the time of screening to ensure that the entire population of antibodies within the library is accurately represented on the phage surface.

The vector encoding the secreted protein or coat protein-fusion protein may include a translational termination codon at the junction of the exoprotein and coat protein coding regions. When expressed in a bacterial cell carrying a corresponding translation termination suppressor, the fusion protein is produced. When expressed in a bacterial cell without the corresponding suppressor, free exoprotein is not produced.

Method of Using the Invention

When the mutant secretion signal sequences of the invention are used in the construction of a vector for protein expression in a bacterial host cell, e.g. *E. coli*, the polypeptides are secreted into, and recovered from, the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

When the mutant secretion signal sequences of the invention are used in the construction of a phage vector or phagemid vector for the expression of a fusion protein which is an exoprotein fused to a phage coat protein, the protein is assembled on the surface of a phage particle formed and secreted from a host cell membrane, e.g. an *E. coli* cell.

Using the phage vectors exemplified herein as a starting point, the proteins or exoprotein-phage coat protein fusion can be variegated at specific, discrete residue positions or at regions such as N-linked glycosylation sequence, commonly referred to as an NXT sequence, using directed mutagenesis to generate a library of molecules. Particularly useful is a modified Kunkel mutagenesis method which can be used to generate billions of *E. coli* colonies each harboring a different exoprotein sequence. While efficient, the percentage of non-mutagenized parental DNA increases when generating highly complex sequence libraries. In addition, technical limitations of synthesis of long oligonucleotides can reduce the effectiveness of the method when used to make libraries containing sequence diversities in distant regions. To overcome these limitations, additional techniques of generating oligonucleotides greater than 350 bases can be used. These techniques include use of a mega-primer and creation of a stem-loop sequence containing a restriction enzyme recognition site in the mutagenesis template in combination with the standard Kunkel mutagenesis method (Kunkel at al. 1987 Methods Enzymol. 154: 367-382) as described in US20050048617. Compared to other library technologies, such as restriction cloning (Marks et al., 1991 J. Mol. Biol. 222:581-597; Griffiths et al. 1994 EMBO J. 13, 3245-3260; Hoet et al. 2005 Nature Biotechnol 23, 344-348), phage recombination (Gigapack, Invitrogen), and sequence specific recombination, the improved Kunkel based method is significantly more effective in generating a sequence diverse library (greater than $10^9$) and is more versatile for introducing sequence diversity in any location in the targeted DNA.

The display of an Fc-containing protein on filamentous phage is particularly useful where it is desired to screen a large population of such molecules for desired binding characteristics. Bacterial cells expressing the desired protein or protein fusion are infected with an M13 variant which allows for preferential packaging of vector DNA carrying the fusion gene into phage particles. Each resulting phage particle displays one or more copies of the fusion protein and contains a vector which encodes the fusion protein. The population of such phage particles can be enriched for desired binding characteristics by a panning procedure. Typically, desired particles are immobilized on a solid surface coated with an antigen to which the desired phage particles can bind, such as an ELISA plate. The bound particles are collected and used to further infect bacterial cells. The panning procedure is repeated to further enrich for desired binding characteristics.

One approach to screening proteins (e.g., antibody or Fc-containing molecules) recovered from phage libraries is to remove the phage coat protein that is linked to the protein molecule for display. To facilitate removal of the phage coat protein, an enzymatic cleavage site may be encoded between the exoprotein and the coat protein and appropriately positioned to include or exclude the tag, e.g. Flag or hexahis, sequences.

Phage and other antibody display methods afford the opportunity to manipulate selection against the antigen or receptor target in vitro. One particular advantage of in vitro selection methods is the ability to manipulate selection procedures to obtain antibodies binding to diverse sites on the target protein. Alternatively, whole cells may be used to select binders.

Phage libraries simplify the retrieval of genetic material associated with functional attributes; however, multistep panning strategies are required to isolate the best candidate from the library. Domain or epitope directed pannings have become a routine way of selecting antibodies that bind to a target protein. Such selections have primarily been achieved by employing a stepwise selection of antibodies utilizing methods known variously as selective panning, de-selective panning, ligand capture, subtractive panning or pathfinder selection.

In subtractive panning, target(s) with overlapping but not completely identical binding sites can be used to de-select unwanted binders. This strategy has been used to identify binders even to unknown antigens as in the use of normal cells to de-select binders to cancer cells. Alternatively, naturally occurring proteins with some common domains or structure are used in sequential or competition selection to obtain antibodies binding to sites that differ or are common among the related antigens. In some cases, naturally occurring proteins such as related chemokines or a mutated version of a protein can be used in subtractive panning.

Ligand-capture directed panning is analogous to an ELISA sandwich assay in that an immobilized antibody to an irrelevant and non-adjacent epitope is used to capture and present the preferred binding face of the target ligand for phage panning (U.S. Pat. No. 6,376,170). Others have used competing antibodies to selectively mask the antigen at other than the desired target domain (Tsui, P. et al. 2002. J. Immunol. Meth. 263:123-132). Pathfinder technology uses monoclonal and polyclonal antibodies, as well as natural ligands conjugated directly or indirectly to horseradish peroxidase (HRP). In the presence of biotin tyramine these molecules catalyze biotinylation of phage binding in close proximity to the target antigen, allowing specific recovery of 'tagged' phage from the total population using streptavidin. In this way, phage binding to the target itself, or in its immediate proximity, are selectively recovered (Osborn, J. K. et al. 1998. Immunotechnol. 3: 293-302). These methods, variations of the methods, and other methods known to those skilled in the art may be employed to query the libraries of exoproteins generated using the expression methods relying on the mutant secretion signals of the present invention.

In one embodiment, the phage library is used to screen variants of the Fc-portion of the molecules for enhanced, decreased, or altered binding to natural or recombinant Fc-receptors, such as FcRgammaIII (CD16), FcRgammaII (CD32), and FcRgammaI (CD64).

While having described the invention in general terms, the embodiments of the invention will be further disclosed in the following examples that should not be construed as limiting the scope of the claims.

Example 1

Multivalent Peptide Display on pVII

To test if pVII can efficiently and stably display multi-copy of different peptides and proteins, a phage genomic display vector was designed and constructed. The pVII vector was constructed using the phage genome M13KE, a derivative of M13mp19 (vectors which are derivatives of the single-stranded, male-specific filamentous DNA bacteriophage M13, NCBI NC_003287, and approximately 7250 bp in length). The pVII and pIX coding sequences lie adjacent to one another in the genome. In this vector, the peptide with a start codon and a GSGGG linker was inserted into the N-terminus of pVII (FIG. 1A). The BsrG I restriction endonuclease site before the pVII coding region and the BspH I site at the end of pIX coding region were used for cloning.

A series of biochemically diverse peptides including a linear peptide (HA), heavily negative charged peptide (Flag), positively charged (6xHis tag), and disulfide bond constrained peptides (PHPEP 190, PHPEP 97) were cloned into this vector and tested (Table 1). The DNA fragment coding for signal sequence, peptide, GS linker, pVII and pIX, and flanking DNA sequences on 5' and 3' ends stretching to BsrG I and BspH I recognition sites, was generated by overlap PCR. The gel-purified PCR product was digested with BsrG I and BspH I restriction endonucleases and then was ligated into double-strand M13KE phage DNA digested with the same enzymes. The ligated recombinant phage DNA was transformed into XL1-Blue E. coli competent cells (Stratagene).

TABLE 1

Peptide sequences displayed on pVII

| SEQ ID NO: | Peptide Name | Sequence |
|---|---|---|
| 5 | HA | YPYDVPDYA |
| 6 | FLAG | DYKDDDDK |
| 7 | 6xHis | HHHHHH |
| 8 | PHPEP 190 | GGDPCTWEVWGRECLQGG |
| 9 | PHPEP 97 | RECHPQNWTSCSN |

The transformed cells were then plated on a lawn of XL1-Blue host cells to isolate single plaques. Phage plaques on XL1-Blue E. Coli lawn were resuspended in Phosphate-buffered saline (PBS) to allow the phage particles to diffuse from top agar. The diffused phage was added to XL1-Blue liquid media and grown to O.D. 0.5 to infect the E. coli cells. The culture was shaken for 5 hours at 37° C. After shaking the bacteria were removed by centrifugation. The phage particles in the supernatant were precipitated by adding one-tenth volume of cold 0.5 M sodium chloride, 4% PEG-800 and incubating the mixture at 4° C. for 3 hours. The mixture was centrifuged and the phage pellet was resuspended in PBS, aliquotted and stored at −20° C.

Assays of whole phage binding to immobilized ligands on microtiter plates (phage ELISA), DNA sequencing and titration of phage titer were used to characterize the phages and evaluate their displaying on the phage surface. Black Maxisorp ELISA plate (NUNC) was coated overnight with 100 μL/well of antibody or protein recognizing displayed peptide at the concentration of 5 ug/mL in the carbonate coating buffer, pH 9.5. The coated plate was washed 3 times with Tris-buffered saline containing 0.1% Tween-20 (TBST) and blocked with Chemiblocker (Chemicon International) at RT for 1 hour. Phage samples, diluted in Chemiblocker, were added to the plate for binding. After 1 hr of incubation at RT, the plate was washed again to remove the unbound phage. The detection antibody, anti-M13/horseradish peroxidase conjugate (GE healthcare), was diluted 1:5,000 in TBST/10% Chemiblocker and added to the plate at 100 ul/well and incubated for 1 hour at RT. After the final wash, the POD chemiluminescent substrate (Roche) was added to the plate, 100 μl/well, for detection and the plate was read immediately on a Tecan plate reader.

Results

The phage ELISA data is shown in FIG. 2A-E, demonstrating that all five peptides were successfully displayed on the phage surface tethered to pVII coat protein, despite having varying structures and biophysical properties.

Figure 3:
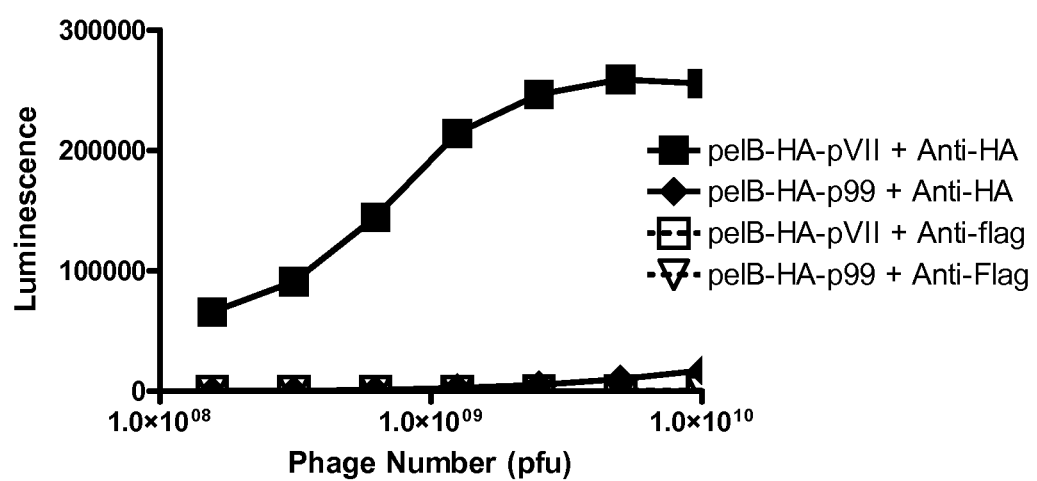
FIG. 3 shows the results of an ELISA on phages derived from the HA-pVII phage vector (FIG. 1A) as compared with the display on phages derived using a hybrid vector for display of HA tethered to pIX where anti-HA was used for specific detection and anti-flag antibody was used as the control antibody for the experiment.

A phage vs. phagemid display comparison is shown in FIG. 3, where the penta-valent display phage system (with all five copies of pVII displaying fusion protein) is compared with the result from a hybrid display system (phage vector having both wild type and fused pIX coding sequences, p99, as described in WO2009/085464 and WO2009/085468) on pIX in which only one copy of the peptide in average was displayed. The ELISA result demonstrated that the HA peptides displayed on the phages derived from the pVII phage vector bound to the anti-HA antibody dramatically better than the phages derived from the p99 hybrid system, suggesting that the vector system produced a multivalent phage display.

Example 2

Effect of Secretion Signals on Peptide Display

Wild-type pVII is naturally synthesized without a signal peptide despite the fact that it is an inner membrane protein in the host cell. However, in previous studies of pVII and pIX display systems, a signal peptide was used (Gao, et al. 1999, Proc Natl Acad Sci USA 96-6025; Kwasnikowski et al. 2005 Journal of Immunological Methods 307:135-143). To examine whether the bacterial signal sequence is necessary for phage display on pVII, we created constructs in which pelB was either added or not added in front of the HA peptide followed by GSGGG linker and pVII.

Figure 4:
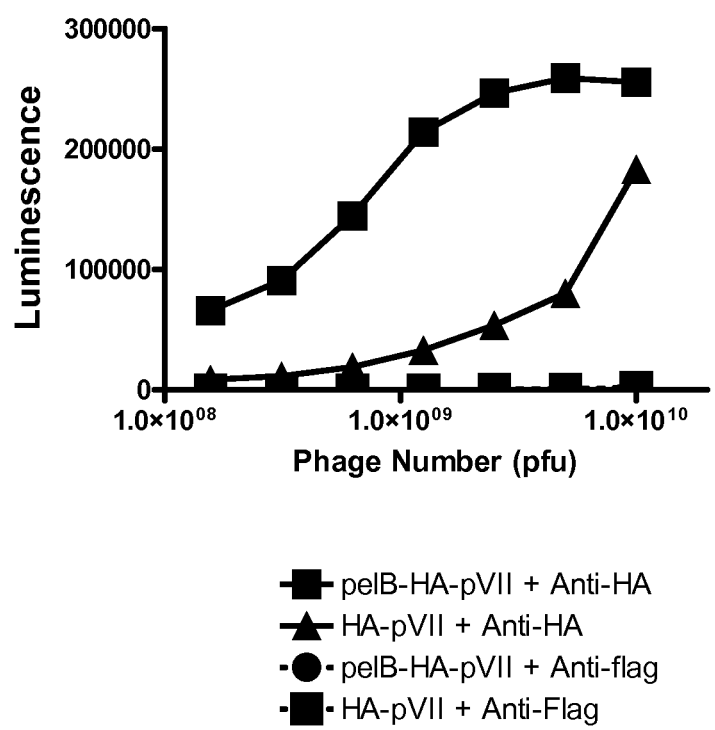
FIG. 4 shows the display of HA peptide on the phages derived from the pVII phage vector with (pelB-Ha-pVII) or without (HA-pVII) pelB signal sequence was compared. Anti-flag antibody was used as the control antibody in this experiment.

FIG. 4 showed that HA could be displayed on phage surface without pelB. However, HA was significant less efficiently displayed on the phage surface as indicated by the weaker ELISA signals, even though the number of phage particles used was the same as those for the phages with pelB (FIG. 4). The ELISA data suggested that the signal sequence pelB, although not necessary, improved peptide display presumably by helping bring the HA fused pVII peptide into the membrane, where phages were assembled. A time course study of phage growth indicated that the phages derived from the phage vector with pelB grew faster than from that without pelB (data not shown), provided further evidence that the bacterial signal peptide helped the assembly of phage with HA displayed on the surface.

Example 3 pelB Mutation

PHPEP 97 (RECHPQNWTSCSN), a disulfide bond constrained 13 amino acid peptide which binds to streptavidin, was among the peptides tested for the pVII phage display (Example 1). In the phage ELISA, two clones of PEP97 (CL #7 and CL #8) showed elevated binding capacity to streptavidin (FIG. 2E). Sequence analysis of these clones revealed a single amino acid mutation Pro6 to Ser (FIG. 5A) in the pelB sequence of both clones.

The P6S pelB was then tested for its ability to enhance display of other peptides and improvement of display efficiency was also observed (data is not shown). To test whether the mutation affected protein secretion, pelB or mutated pelB was fused to alkaline phosphatase (AP) and the secretion of AP in DH10B bacteria examined.

The secreted alkaline phosphatase activity in cell culture was determined. The results showed, in FIG. 6A, that indeed the mutation significantly improved the AP secretion into the cell medium (supernatant fraction) although the AP concentration inside of cells was the same (FIG. 6B). We therefore hypothesized that the mutated pelB improved the translocation of PHPEP97-pVII to the membrane where phage was assembled by this mutation. To our knowledge, there have been no other reports of mutation in pelB that increase the protein secretion.

Example 4

Dual Multivalent Display of Peptides on Phage pVII and pIX

To multivalently display two different peptides simultaneously, a phage vector was constructed based on the phage genome M13KE, in which the mutant P6S bacterial signal peptide pelB (SEQ ID NO: 2, C16T), peptide A, and the flexible GSGGG linker were inserted to the N-terminus of the pVII gene; the wild type bacterial signal peptide ompA (SEQ ID NO: 4, G31), peptide B and a flexible GSGGG linker were inserted into the N-terminus of pIX (FIG. 1B). The BsrG I restriction endonuclease site before the pVII coding region and the BspH I site at the end of pIX coding region were used for cloning. The DNA fragment coding for signal sequences, peptides, GS linkers, pVII, pIX genes and flanking DNA sequences on 5' and 3' ends stretching to BsrG I and BspH I recognition sites, was generated by overlap PCR. The gel-purified PCR product was digested with BsrG I and BspH I restriction endonucleases and then was ligated into double-strand M13KE phage DNA digested with the same enzymes. The ligated recombinant phage DNA was transformed into XL1-Blue E. coli competent cells (Stratagene) and the transformed cells were plated on a lawn of XL1-Blue host cells to isolate single plaques as before.

Figure 7:
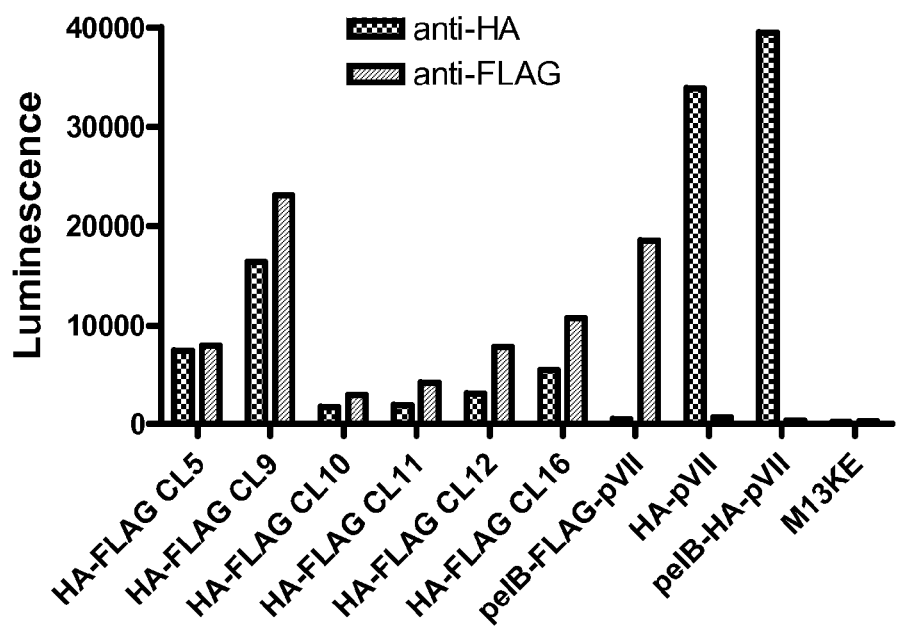
FIG. 7 shows the results of a phage ELISA assessing the dual display of HA and FLAG peptides on pVII and pIX of the same phage particle: six FLAG-pVII-HA-pIX phage clones were tested for binding density with anti-FLAG and anti-HA antibodies using HA-pVII, FLAG-pVII and M13KE phages as control.

The display of both FLAG and HA peptides was evaluated by phage ELISA (FIG. 7) which demonstrated that both peptides were displayed on the phage particles. As was the case for the display of PHPEP 97, however, the original plaque size was very small and the phage titer was low.

Figure 8:
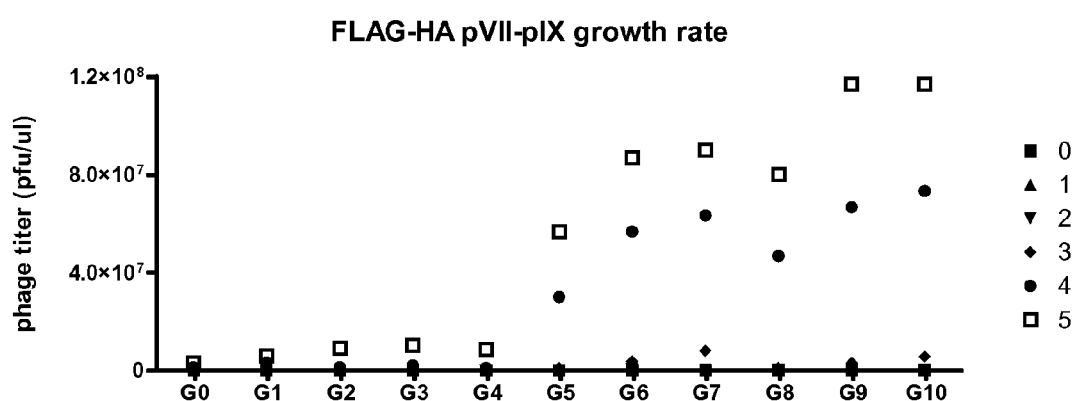
FIG. 8 shows the titer at six times points indicating the improvement growth rate of a single clone during continuous multiple round passages (generations G0-G10) in which the mutant ompA signal was discovered.

To select for the spontaneous mutations in the phage that could improve the growth rate, we continuously passed the phage from two individual clones. After five rounds of continuous passages, a significant increase of the phage titer of one clone (#11) was observed over time (FIG. 8). A comparison of the sequence of the whole phage genome purified from round 5 and round 10 phages identified only one single amino acid mutation, Ala to Pro, located on the position 11 of the signal peptide ompA (FIG. 5B). The same mutation was identified from the phages of the other clone (#9). The mutation, however, did not significantly affect the secretion of alkaline phosphatase as had the mutation in pelB (FIG. 6A).

Example 5

Full IgG Display on Phage Particles

A. Vector Design

Figure 9:
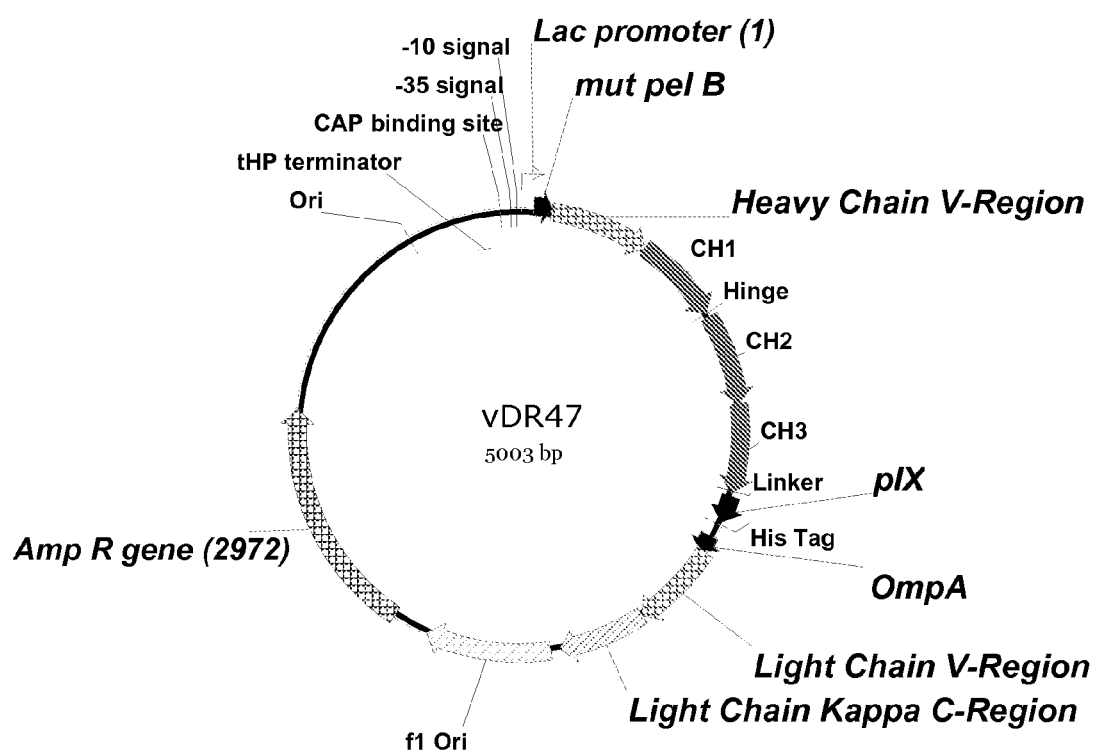
FIG. 9 shows a schematic of the phagemid vector constructed for expression of full human IgG using the P6S pelB variant as a secretion signal linked to the heavy chain and where the heavy chain C-terminus was fused via linker to the pIX coat protein and the light chain, fused to ompA secretion signal, was expressed as a free polypeptide.

The full IgG display phagemid (vDR47, FIG. 9) was constructed starting from the phagemid construct as described in WO2009/085462 (pCNTO Fab IX). Sequences encoding a human IgG1 hinge, CH2 and CH3 domains were added as well as the P6S pelB variant signal sequence, and the vector does not have a lacI gene however the expression could be controlled by a lac promoter.

B. Characterization of Constructs Used for Full IgG Display

A panel of test constructs was made to assess the display of full IgG on pIX. Antibodies to IL13, designated 6-2 and 16-7, and an anti-cytokine antibody 9-4 were chosen as prototypes for constructing the new full IgG molecules. To determine the effect of different codon usage, two constructs were made for each of the anti-IL13 antibodies, one with human codon optimization and one with E. coli codon optimization. Table 1 lists the vector designation for the five full IgG test constructs. Optimized genes were synthesized and assembled into double stranded DNA as described in U.S. Pat. Nos. 6,670,127 and 6,521,427. In addition, an EMP-1 peptide-Fc fusion construct (CNTO530, SEQ ID NO: 88 of U.S. Pat. No. 7,393,662) fused to pIX was included as a control as it contains the human IgG hinge, CH2 and CH3 domains but no light chains.

TABLE 2

Test constructs for full IgG Display

| pDR# | Isotype | Codon Usage | Description | Antigen Specificity |
|---|---|---|---|---|
| pDR2129 | huIgG1/HuKappa | Human codon | 6-2 full IgG | Human IL13 |
| pDR2130 | huIgG1/HuKappa | Human codon | 16-7 full IgG | Human IL13 |
| pDR2131 | huIgG1/HuKappa | E. coli codon | 6-2 full IgG | Human IL13 |
| pDR2132 | huIgG1/HuKappa | E. coli codon | 16-7 full IgG | Human IL13 |
| pDR3041 | huIgG1/HuKappa | Human codon | 9-4 full IgG | Human IL17A |

C. Phage Production

The full IgG display constructs described in section B above were transformed into two different F' E. coli strains, TG-1 and XL-1 blue, according to standard protocols. The reason for testing these two strains is their difference in growth rate, which hypothetically could affect the packaging and display of the full IgG pIX fusion protein. Individual transformants were picked and grown over night in 2XYT media supplemented with Carbenicillin (always used at 100 µg/ml). The overnight culture (500 µl) was then used to inoculate 25 ml 2XYT/Carbenicillin and the culture was grown at 37° C., 250 rpm, until OD (600 nm) reached 0.5. The bacteria were infected with $10^{11}$ pfu/ml of VCSM13 helper phage (Stratagene, La Jolla, Calif.) during a 30 min incubation at 37° C. with no shaking followed by a centrifugation step at 3,000 rpm for 15 minutes. At this step, the standard protocol calls for the induction of the bacterial culture with 2XYT/Carbenicillin/IPTG (1 mM). However, we divided the cultures into two and added 1 mM IPTG to one and not to the other, with the hypothesis that the leakiness of the system would suffice to produce the fusion protein with subsequent phage packaging. In summary, for each construct, four different phage preparations were made: (i) TG-1 with IPTG (ii) TG-1 without IPTG (iii) XL-1 blue with IPTG (iv) XL-1 blue without IPTG. The cultures were grown over night at 30° C. at 250 rpm and the next day, spun down at 3,000 rpm for 15 minutes, followed by the precipitation of the phage supernatant in PEG/NaCl. After 2 h on ice, the precipitated phage were spun down at 10,000 rpm, 15 min, and the phage pellet was resuspended in 2 ml PBS. The phage preparation was further clarified of any remaining bacterial pellet by a spin at 10,000 rpm for 10 min and stored in 2 ml tubes at 4° C.

D. Phage Titers

The phage titers were determined according to standard protocols. Briefly, TG-1 cells were grown in 2XYT until OD (600 nm) reached 0.5. Phage preparations were serially diluted in PBS in a 96 well plate and TG-1 cells were added to the phage and incubated at 37° C. to allow infection. After 30 min, a spot titration was carried out by dispensing 2 ul of each well onto LB agar plates containing 1% glucose and Carbenicillin. The plates were incubated at 37° C. overnight and the phage concentration in terms of colony forming units (cfu) per ml was determined Table 3 shows the results from the phage titration for all of the constructs and culture conditions. All clones produced high phage titers, between $10^{11}$-$10^{11}$ cfu/ml which were in the expected range and indicated that phage was produced efficiently.

TABLE 3

| Description | pDR vector | Lac inducer | TG-1 | XL-1 Blue |
|---|---|---|---|---|
| 6-2 IgG Human Codon | 2129 | −IPTG | 1.00E+13 | 2.00E+13 |
| | | +IPTG | 5.00E+12 | 5.00E+12 |
| 16-7 IgG Human Codon | 2130 | −IPTG | 2.00E+13 | 2.00E+13 |
| | | +IPTG | 2.00E+12 | 2.00E+12 |
| 6-2 IgG E Coli Codon | 2131 | −IPTG | 2.00E+13 | 2.00E+13 |
| | | +IPTG | 2.00E+13 | 2.00E+13 |
| 16-7 IgG E Coli Codon | 2132 | −IPTG | 2.00E+12 | 5.00E+12 |
| | | +IPTG | 1.00E+11 | 5.00E+11 |
| EMP-1 Fc Construct | 2467 | −IPTG | 2.00E+13 | 2.00E+13 |
| | | +IPTG | 2.00E+12 | 2.00E+12 |

E. IgG Domain-Specific Sandwich ELISAs to Assess Functional Display

In order to assess the display of the full IgG molecule on phage pIX, a series of sandwich ELISAs were set up. Black maxisorp plates were coated with 1 µg/ml of one of the following capture antibodies diluted in TBS; sheep anti-human IgG (Fd, CH1) antibody (The Binding Site, Birmingham, UK), mouse anti-human kappa light chains (Southern Biotech, Birmingham, Ala.), mouse anti-human IgG (CH2 domain) antibody (AbD Serotec, Raleigh, N.C.), and mouse anti-human IgG (CH3 domain) antibody (AbD Serotec). After blocking the plates with Chemiblocker (Chemicon/Millipore, Billerica, Mass.), plates were washed and phage were added at a concentration of 2×10^11 cfu/ml (diluted in 10% chemiblocker/TBST) and incubated for one hour. Plates were washed and HRP conjugated mouse anti-M13 antibody was added to the plates. After a 30 min incubation, plates were washed and Chemiluminescence substrate was added to the wells and the plates were read in the Envision plate reader. FIGS. 10A-D show the results from the CH1 (FIG. 10A), Kappa (FIG. 10B), CH2 (FIG. 10C) and CH3 (FIG. 10D) sandwich ELISAs, respectively. Controls used in the ELISAs were phage displaying the Fab-pIX fusion of clone 6-2 in vDR10 (human codon optimized, made in TG-1 cells, with IPTG induction), an nonspecific scaffold protein-pIX fusion, or the CNTO530-pIX fusion. In the CH1 and Kappa ELISAs, the 6-2 Fab serves as a positive control, whereas the EMP-1 construct (CNTO530) molecule serves as a negative control. In the CH2 and CH3 ELISAs, the 6-2 Fab serves as a negative control and the CNTO530 molecule as a positive control. The scaffold protein phage serves as a negative control in all ELISAs since it does carry any antibody domains. The ELISAs assays were also performed with the addition of an anti-IL13 full IgG1 antibody as a soluble competitor at a concentration of 5 ug/ml in order to prevent binding of the phage to the different capture antibodies.

Figure 10A:
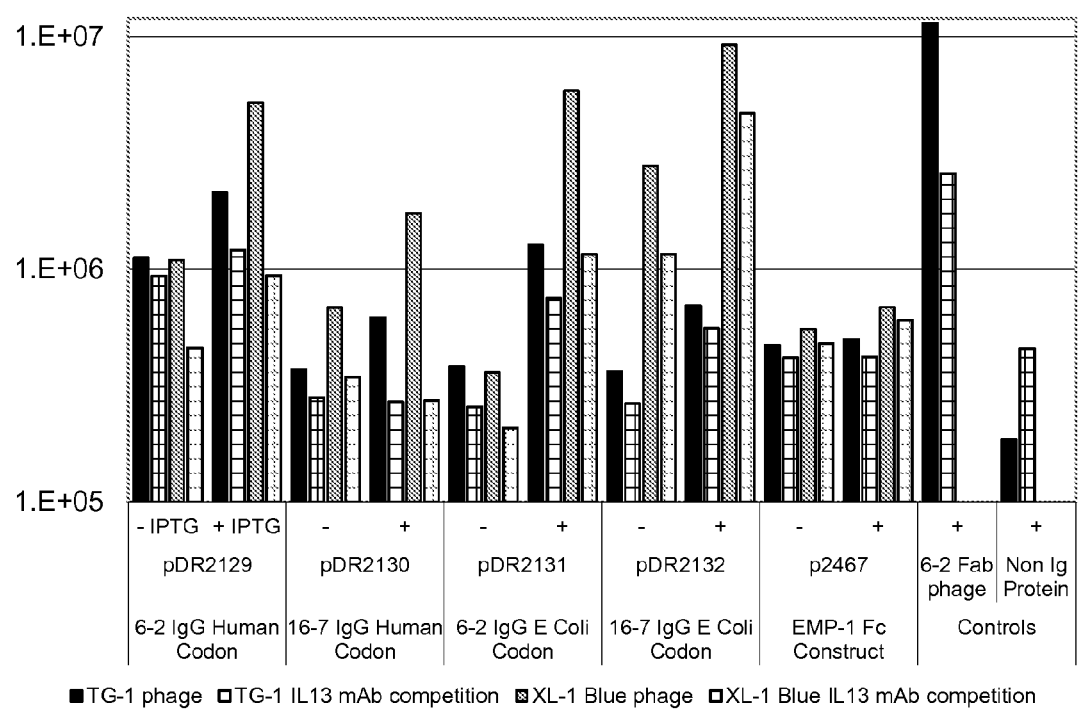
FIG. 10A-D are column graphs showing the signal produced for in an ELISA format for phage captured from the indicated preparations using various ligands specific for either antibody domains expressed on the phage, an expressed EMP-1-Fc construct, or the phage itself: (A) Anti-Fd (CH1) antibody capture; (B) anti-kappa antibody; (C) anti-CH2 antibody; and (D) anti-CH3 antibody. The 6-2 Fab pIX on phage and the non-immunoglobulin protein on phage are included as negative controls.
Figure 10B:
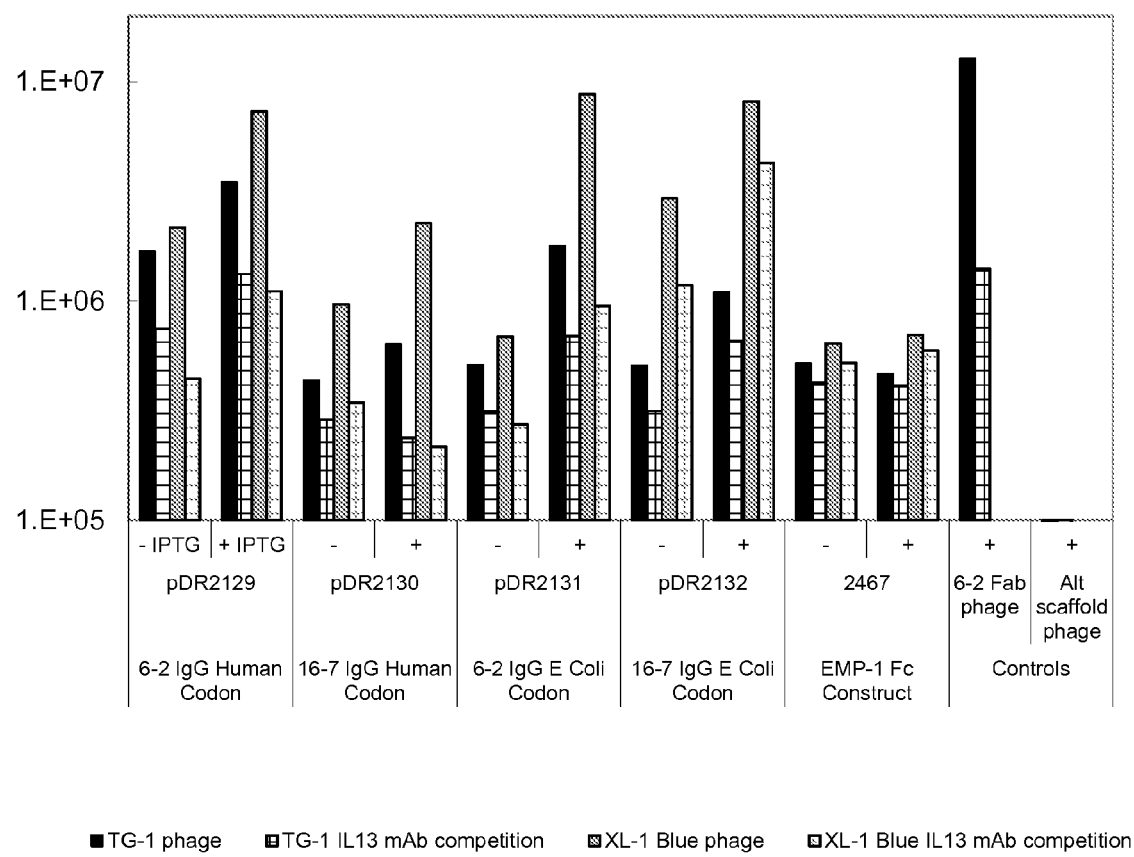
Figure 10C:
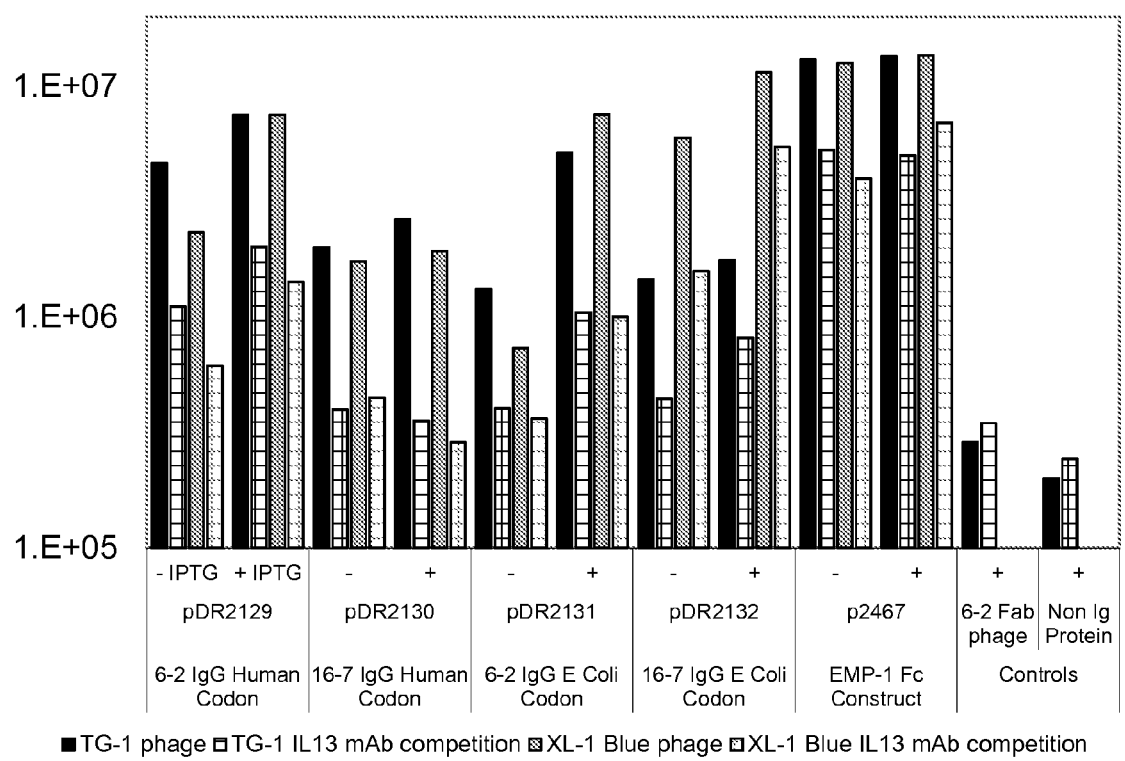
Figure 10D:
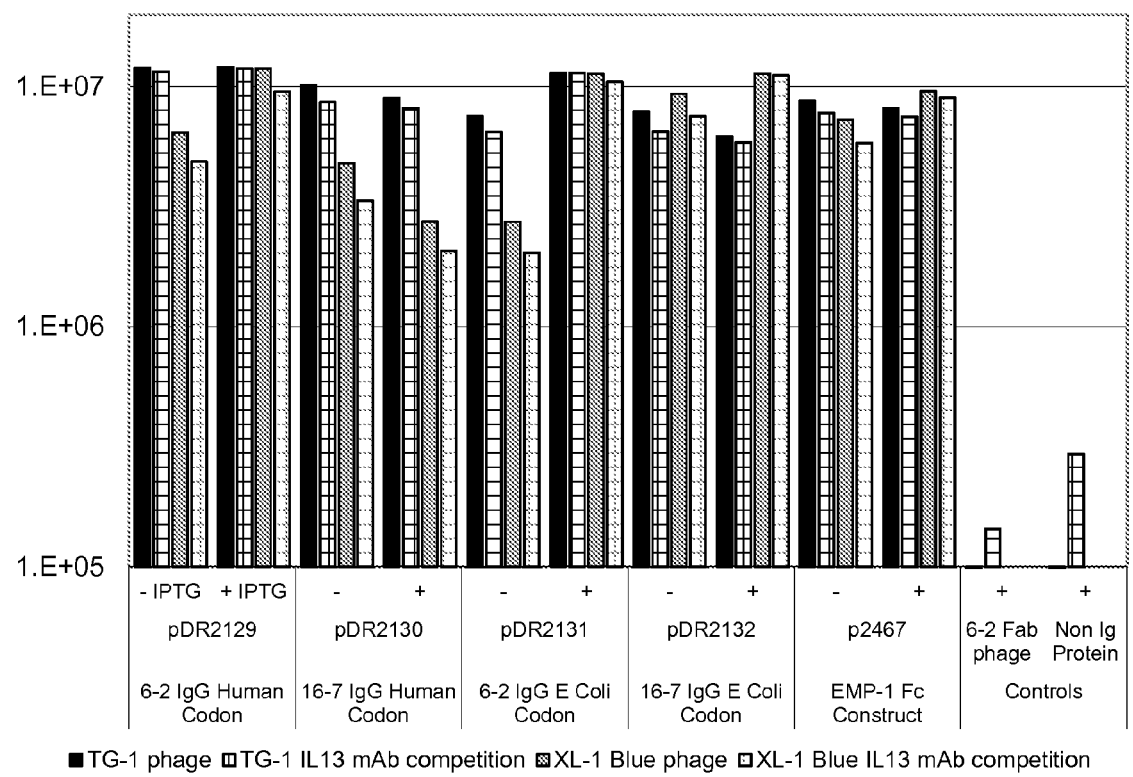

As shown in FIGS. 10A-D, phage can be detected in all of the sandwich ELISAs, providing evidence that the phage were in fact displaying the different antibody domains on the surface. Phage produced in XL-1 blue cells had the highest signals and the addition of IPTG had a positive effect on the binding signal. The binding of phage can be inhibited by the addition of the soluble anti-IL13 antibody, which indicates specific interactions. However, the soluble anti-IL13 antibody could not compete off the interaction between phage and the CH3 domain (FIG. 10D). This was observed for both the full IgG-pIX fusions as well as for the EMP-1-Fc-pIX fusion (CNTO530).

F. Full IgG pIX Phage Binding to IL13

Figure 11:
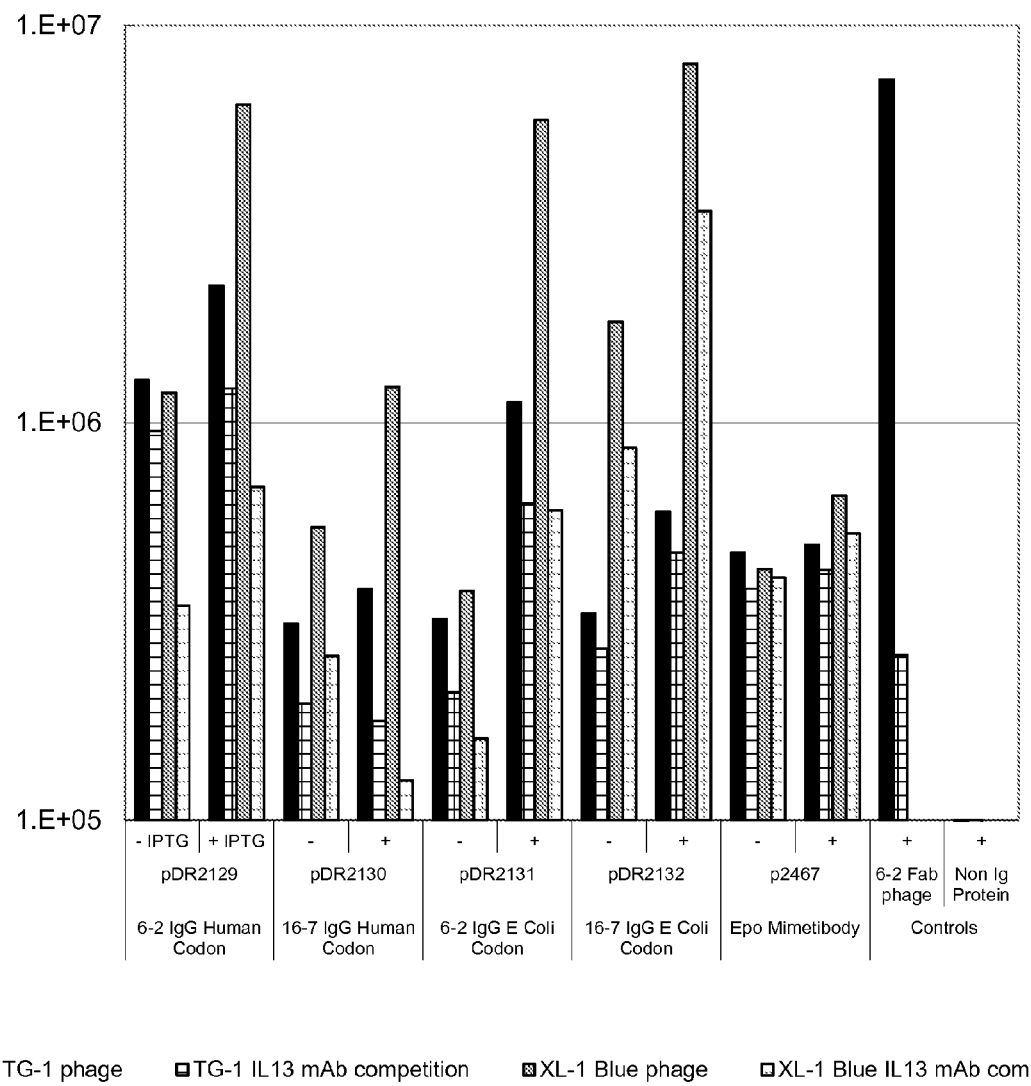
FIG. 11 is a column graph showing the signal produced for in an ELISA format for phage captured from the indicated preparation using commercial anti-IL13 antibody and in the presence or absence of a competing soluble anti-IL13 mAb with the same specificity as the anti-IL13 IgG pIX (checkered bars). The EMP-1-Fc construct is a negative control does not bind IL13 and the IL13 specific 6-2 Fab pIX on phage is included as positive control.
Figure 12A:
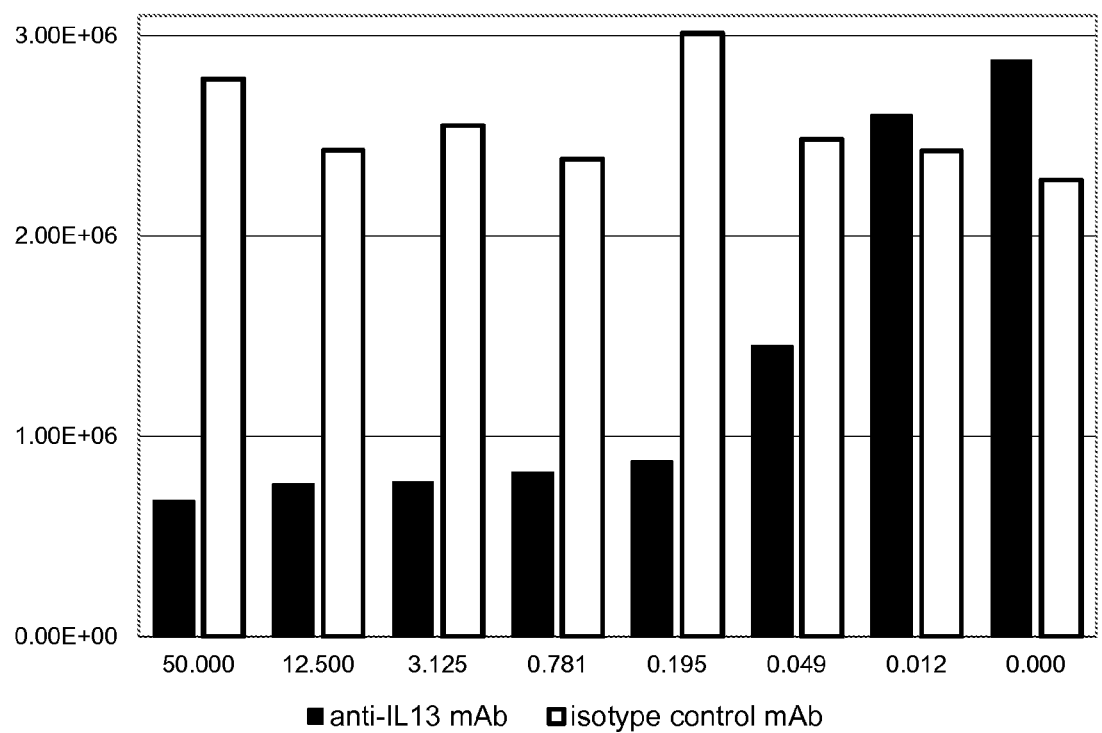
FIG. 12A-B are column graphs showing the signal produced for in an ELISA format for phage captured in plates by a commercial anti-IL13 antibody followed by the addition of increasing amounts of a competing anti-IL13 antibody (6-2 full IgG) on phage or a control antibody not specific for IL13 (anti-EMMPRIN) (A) and by IL13 captured in plates by a commercial anti-IL13 antibody followed by the addition of 6-2 Fab on phage. Increasing amounts of either an anti-IL13 mAb or an anti-EMMPRIN mAb was added (B).
Figure 12B:
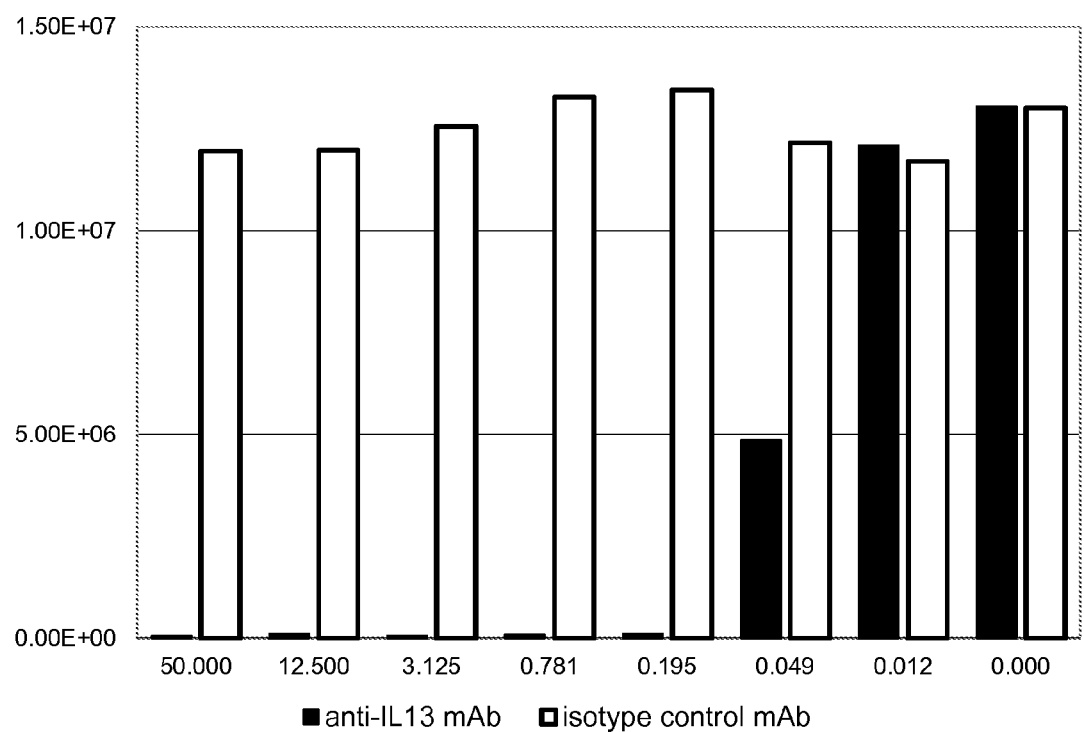

After demonstrating that all domains of the IgG molecule can be detected on the phage particles by the ELISAs, it was necessary to determine if the constructs also retained the ability to bind to their respective antigen. The IL13 binding ELISA was set up by coating black Maxisorp plates with 1 ug/ml of a commercial anti-IL13 antibody (mouse anti-human IL13, MAB213, R&D Systems). The MAB213 does not compete with 6-2 or 16-7 for binding to IL13 and thus is ideal as a sandwich ELISA capture antibody. After washing and blocking, biotinylated human IL13R130Q human (Peprotech) was added at 100 nM and incubated for one hour. Plates were washed and phage displaying full IgG versions of 6-2 and 16-7 on pIX were added at $2 \times 10^{11}$ cfu/ml, either alone or together with a soluble anti-IL13 antibody for competition. Bound phage was detected with HRP-conjugated mouse anti-M13 antibody and chemiluminescence was read in the Envision instrument. FIG. 11 shows the result of the IL13 phage ELISA. Binding is detected in most conditions, with phage produced in XL-1 blue cells with 1 mM IPTG showing the highest signals. The peptide-Fc-pIX and alternative scaffold molecule-pIX fusions were negative, as expected, and the 6-2 Fab pIX control was positive. The binding was inhibited by adding soluble anti-IL13 antibody, showing that the interaction is specific. To further examine the IL13 binding, an ELISA was set up in which the soluble competition antibody was serially diluted from 50 μg/ml-0.01 μg/ml. A control antibody was also included. FIGS. 12A and B show the effect of soluble antibody competition on IL13 binding of 6-2 IgG pIX and 6-2 Fab pIX, respectively. Inhibition of binding is seen for both constructs, with an IC50 of approximately 0.1 μg/ml. However, for the full IgG pIX construct, the inhibition is incomplete even at very high competitor concentrations, suggesting that some level of un-specific interactions is present.

G. Full IgG pIX Phage Binding to IL13 and IL17

Figure 13:
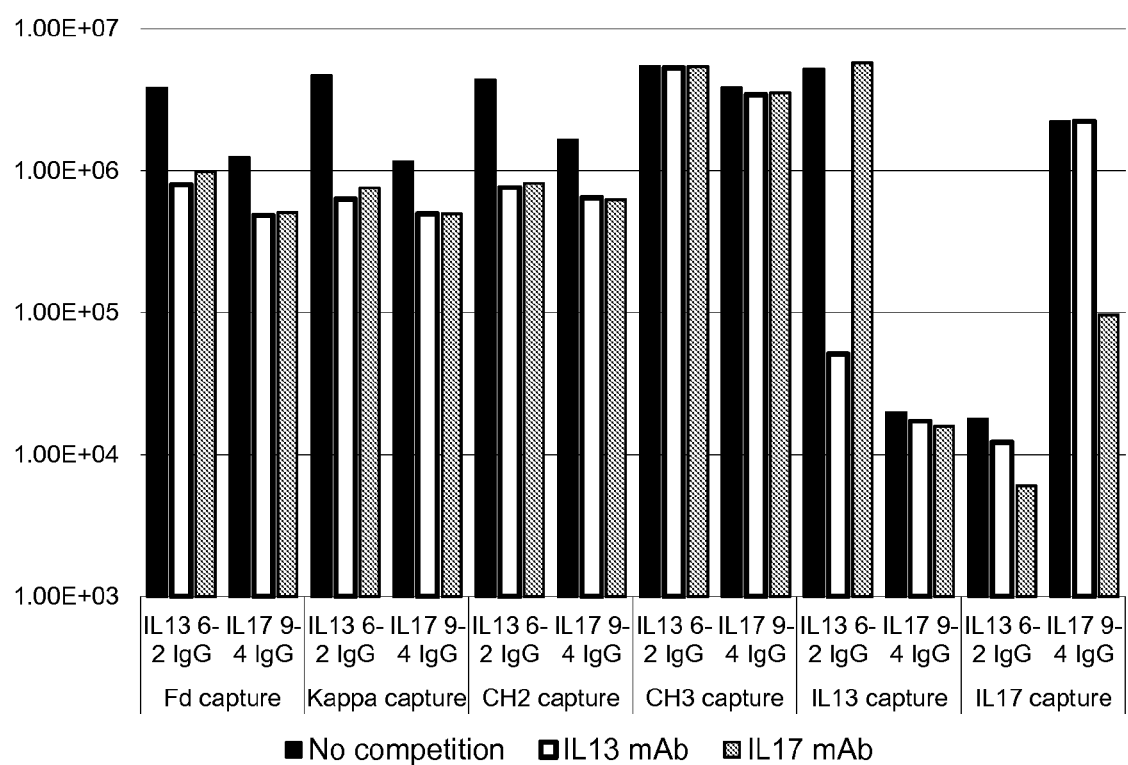
FIG. 13 shows a signal from phage was captured by either of the domain specific antibodies anti-Fd, anti-Kappa, anti-CH2 and anti-CH3 after biotinylated IL13 or IL17A antigens were used to capture phage displaying full IgG constructs of IL13 or IL17A and in the presence or absence of competing soluble anti-IL13 mAb or anti-IL17A mAb. The phage were detected with anti-M13 antibody (y-axis).

A second confirmatory experiment was performed. This was done by cloning a full IgG version of an anti-IL17A antibody. The construct was transformed into XL-1 blue cells and phage was produced as described above. ELISAs were carried out to confirm the display of the IL17 IgG on pIX as well as its binding to human IL17Amut6 antigen as shown in FIG. 13. For each ELISA (Fd capture, kappa capture, CH2 capture, CH3 capture, IL13 capture, and IL17 capture), the phage is either added alone or together with a soluble anti-IL13 mAb or a soluble anti-IL17A mAb. The addition of competitor mAb shows the specificity of the ELISA. As evident in FIGS. 12A and B above, the IL17 IgG is displayed on pIX, although at lower levels than the IL13 IgG. This is consistent with differences in Fab expression levels between these constructs (data not shown). The specificity of antigen binding can be seen since the anti IL13 IgG on phage does not bind to IL17 and the anti IL17 IgG on phage does not bind to IL13. In addition, the binding of each of the two types of phage can be inhibited by their soluble mAb counterparts.

Example X

Display of Fc-Containing Proteins Fused to pVII

Additionally, we have demonstrated that Fc and MIMETIBODY™ proteins could be displayed on the phage surface using a pVII phagemid system.

What is claimed:

1. An isolated polynucleotide encoding a bacterial secretion signal for directing translocation of the protein from the bacterial membrane, selected from the P6S variant of pelB of SEQ ID NO: 1 and the A11P variant of ompA of SEQ ID NO: 3.

2. The isolated polynucleotide of claim 1 operably linked to an exoprotein encoding sequence, wherein the exoprotein is to be secreted from the bacterial membrane.

3. The isolated polynucleotide of claim 2, wherein the exoprotein is further operably linked to a sequence encoding a phage coat protein selected from pIII, pVII, pVIII, and pIX and wherein the fusion protein so formed is to be secreted from a bacterial membrane.

4. The isolated polynucleotide of claim 3, wherein the exoprotein is selected from the group consisting of an polypeptide comprising a peptide, an antibody heavy chain constant domain, an antibody heavy chain, a mammalian receptor chain, a receptor extracellular domain, a fibronectin-like domain, and an ankyrin repeat domain.

5. A vector comprising nucleic acid sequences encoding a bacterial secretion signal operably linked to a polynucleotide encoding an amino acid sequence derived from an exogenous protein, the encoded secretion signal selected from the P6S variant of pelB of SEQ ID NO: 1 and the A11P variant of ompA of SEQ ID NO: 3, wherein said secretion signal enhances the proportion of exoprotein found translocated from the bacterial membrane as compared to the wild type secretion signal.

6. The vector of claim 5 wherein said encoded exogenous protein encoding sequence is further fused to the sequence encoding a filamentous phage coat protein selected from pIII, pVII, pVIII, and pIX.

7. The vector of claim 6 which is a phagemid vector.

8. The vector of claim 6 which is a phage vector.

9. The vector of claim 8 in which an exoprotein encoding sequence linked to a mutant secretion signal is fused to pVII and an exoprotein sequence linked to a mutant secretion signal is fused to pIX thereby causing the both exoproteins to be present as multiple copies on the surface of the phage particle when the vector is replicated in a host cell.

10. The vector of claim 6 wherein the encoded exoprotein is selected from the group consisting of a peptide, an antibody heavy chain constant domain, an antibody heavy chain, a mammalian receptor chain, a receptor extracellular domain, a fibronectin-like domain, and an ankyrin repeat domain.

11. The phage vector of claim 5, further comprising an inducible promoter.

12. The phage vector of claim 11, wherein the inducible promoter is a lac promoter or mutant of lac.

13. A filamentous phage particle encapsulating a polynucleotide according to claim 3 encoding a secretion signal operably linked to an exoprotein, and having said exoprotein on a surface of said phage.

14. The filamentous phage particle of claim 13, wherein the exoprotein is fused to an amino terminus of a filamentous phage pVII or pIX protein, whereupon when the protein is expressed at the surface of a filamentous phage protein, a cysteine residue within one exoprotein becomes oxidatively bonded to a cysteine residue on a second exoprotein expressed on the surface of the same filamentous phage particle and forms a functional protein structure.

15. The filamentous phage particle of claim 14, wherein the functional protein structure comprises an antibody Fc region.

16. The filamentous phage particle of claim 15, wherein the functional activity of the protein structure is FcRn binding.

17. A bacterial host cell comprising a filamentous phage according to claim 13.

18. A phage library of bacterial host cells comprising a filamentous phage vector according to claim 17.

19. The phage library of claim 14, wherein said each polynucleotide encodes an Fc-forming sequence with an amino acid substitution.

20. The phage library of claim 15 wherein said nucleic acid chain wherein the Fc-forming sequence further comprise a ligand binding domain.

21. The phage library of claim 16 wherein the ligand binding domain is selected from the group consisting of a receptor binding ligand, a receptor extracellular domain, an antibody Fab domain comprising a variable domain and a constant domain, and single chain Fv construct.

22. The phage library of claim 17 wherein said Fab domain comprises sequences that vary one from another at specific residues within the binding domain.

23. A method of expressing an exoprotein in a bacterial host cell using a polynucleotide comprising a coding sequence for the P6S variant of pelB of SEQ ID NO: 1, wherein the exoprotein is recoverable from the media supporting the growth of the bacterial host cell.

24. A method of expressing an exoprotein in a bacterial host cell using a polynucleotide comprising a variant of a bacterial secretion signal according to claim 1, wherein the protein is fused to a filamentous phage coat protein and the titer of phage displaying the protein on the surface of the phage particle is higher than when a wild type bacterial secretion signal is used or when no bacterial secretion signal is used.

* * * * *

SEQUENCE LISTING

```
<160> NUMBER OF SEQ ID NOS: 9

<210> SEQ ID NO 1
<211> LENGTH: 22
<212> TYPE: PRT
<213> ORGANISM: Erwinia carotovora
<220> FEATURE:
<221> NAME/KEY: MUTAGEN
<222> LOCATION: (6)..(6)
<223> OTHER INFORMATION: X may be P (WT) or S (variant)

<400> SEQUENCE: 1

Met Lys Tyr Leu Leu Xaa Thr Ala Ala Ala Gly Leu Leu Leu Leu Ala
1               5                   10                  15

Ala Gln Pro Ala Met Ala
            20

<210> SEQ ID NO 2
<211> LENGTH: 66
<212> TYPE: DNA
<213> ORGANISM: Erwinia carotovora
<220> FEATURE:
<221> NAME/KEY: mutation
<222> LOCATION: (16)..(16)
<223> OTHER INFORMATION: c (wt) or t (variant)

<400> SEQUENCE: 2
atgaaatacc tgttgyctac ggcagccgct ggtttgttat tactcgcggc ccagccggcc       60
atggca                                                                  66

<210> SEQ ID NO 3
<211> LENGTH: 21
<212> TYPE: PRT
<213> ORGANISM: Escherichia coli
```

```
<220> FEATURE:
<221> NAME/KEY: MUTAGEN
<222> LOCATION: (11)..(11)
<223> OTHER INFORMATION: X may be A (wt) or P (variant)

<400> SEQUENCE: 3

Met Lys Lys Thr Ala Ile Ala Ile Ala Val Xaa Leu Ala Gly Phe Ala
1               5                   10                  15

Thr Val Ala Gln Ala
            20

<210> SEQ ID NO 4
<211> LENGTH: 63
<212> TYPE: DNA
<213> ORGANISM: Escherichia coli
<220> FEATURE:
<221> NAME/KEY: mutation
<222> LOCATION: (31)..(31)
<223> OTHER INFORMATION: s may be g (wt) or c (variant)

<400> SEQUENCE: 4
atgaaaaaaa ccgcgattgc gattgcggtg scgctggcgg gctttgcgac cgtggcgcag      60
gcg                                                                   63

<210> SEQ ID NO 5
<211> LENGTH: 9
<212> TYPE: PRT
<213> ORGANISM: Artificial Sequence
<220> FEATURE:
<223> OTHER INFORMATION: antibody recognition sequence

<400> SEQUENCE: 5

Tyr Pro Tyr Asp Val Pro Asp Tyr Ala
1               5

<210> SEQ ID NO 6
<211> LENGTH: 8
<212> TYPE: PRT
<213> ORGANISM: Artificial sequence
<220> FEATURE:
<223> OTHER INFORMATION: antibody recognition sequence

<400> SEQUENCE: 6

Asp Tyr Lys Asp Asp Asp Asp Lys
1               5

<210> SEQ ID NO 7
<211> LENGTH: 6
<212> TYPE: PRT
<213> ORGANISM: Artificial sequence
<220> FEATURE:
<223> OTHER INFORMATION: Purification

<400> SEQUENCE: 7

His His His His His His
1               5

<210> SEQ ID NO 8
<211> LENGTH: 18
<212> TYPE: PRT
<213> ORGANISM: Artificial sequence
<220> FEATURE:
<223> OTHER INFORMATION: EGFR-binding peptide

<400> SEQUENCE: 8

Gly Gly Asp Pro Cys Thr Trp Glu Val Trp Gly Arg Glu Cys Leu Gln
1               5                   10                  15
```

```
Gly Gly

<210> SEQ ID NO 9
<211> LENGTH: 13
<212> TYPE: PRT
<213> ORGANISM: Artificial sequence
<220> FEATURE:
<223> OTHER INFORMATION: streptavidin ligand

<400> SEQUENCE: 9

Arg Glu Cys His Pro Gln Asn Trp Thr Ser Cys Ser Asn
1               5                   10
```